(12) United States Patent
Greenberg et al.

(10) Patent No.: US 7,605,128 B2
(45) Date of Patent: Oct. 20, 2009

(54) NEUROGENERATIVE OR NEUROTROPHIC FACTORS FOR MITIGATING A SYMPTOM OF ISCHEMIA

(75) Inventors: David C. Greenberg, Sonoma, CA (US); Kunlin Jin, Novato, CA (US); Xiao Ou Mao, Novato, CA (US); Lin Xie, Novato, CA (US); Yunjuan Sun, Novato, CA (US); Jocelyn Childs, Oakland, CA (US)

(73) Assignee: Buck Institute for Age Research, Novato, CA (US)

( * ) Notice: Subject to any disclaimer, the term of this patent is extended or adjusted under 35 U.S.C. 154(b) by 355 days.

(21) Appl. No.: 10/503,786

(22) PCT Filed: Feb. 14, 2003

(86) PCT No.: PCT/US03/04575

§ 371 (c)(1),
(2), (4) Date: May 2, 2005

(87) PCT Pub. No.: WO03/069310

PCT Pub. Date: Aug. 21, 2003

(65) Prior Publication Data

US 2005/0222022 A1     Oct. 6, 2005

Related U.S. Application Data

(60) Provisional application No. 60/357,310, filed on Feb. 14, 2002.

(51) Int. Cl.
*A61K 38/00* (2006.01)
*A61K 38/18* (2006.01)

(52) U.S. Cl. ........................... 514/12; 435/368; 435/377
(58) Field of Classification Search ........................ None
See application file for complete search history.

(56) References Cited

U.S. PATENT DOCUMENTS

| | | | | |
|---|---|---|---|---|
| 5,851,832 | A * | 12/1998 | Weiss et al. | .................. 435/368 |
| 6,528,245 | B2 | 3/2003 | Sanchez-Ramos et al. | |
| 6,589,728 | B2 | 7/2003 | Csete et al. | |
| 6,737,404 | B2 | 5/2004 | Springer et al. | |
| 6,852,313 | B1 * | 2/2005 | Zsebo et al. | ................ 424/85.1 |
| 2002/0169102 | A1 * | 11/2002 | Frey, II | ............................ 514/1 |
| 2003/0203844 | A1 * | 10/2003 | Delfani et al. | .................. 514/12 |

FOREIGN PATENT DOCUMENTS

| | | |
|---|---|---|
| WO | WO 94/03199 A1 | 2/1994 |
| WO | WO 03/069310 | 8/2003 |
| WO | WO 2007/014156 | 1/2007 |

OTHER PUBLICATIONS

International Search Report dated Dec. 18, 2003 issued in PCT/2003/04575 (WO2003069310).

International Search Report and Written Opinion dated Aug. 9, 2007 issued in PCT/2006/28680 (WO2007014156).

Azizi et al. "Engraftment and migration of human bone marrow stromal cells implanted in the brains of albino rats—similarities to astrocyte grafts." *Proceedings of the National Academy of Sciences U S A*, 95(7): 3908-3913, 1998.

Bjorklund (1992) "Dopaminergic transplants in experimental parkinsonism: cellular mechanisms of graft-induced functional recovery." *Current Opinion in Neurobiology*,2(5): 683-689.

Bjornson et al. (1999) "Turning Brain into Blood: a Hematopoietic Fate Adopted by Adult Neural Stem Cells in Vivo." *Science*, 283(5401): 534-537.

Brazelton et al. (2000) "From Marrow to Brain: Expression of Neuronal Phenotypes in Adult Mice." *Science*, 290(5497): 1775-1779.

Eglitis and Mezey (1997) "Hematopoietic cells differentiate into both microglia and macroglia in the brains of adult mice." *Proceedings of the National Academy of Sciences U S A*, 94(8): 4080-4085.

Fricker et al. (1999) "Site-Specific Migration and Neuronal Differentiation of Human Neural Progenitor Cells after Transplantation in the Adult Rat Brain." *The Journal of Neuroscience*, 19(14): 5990-6005.

Gage (2000) "Mammalian Neural Stem Cells." *Science*, 287(5457): 1433-1438.

Goldman (1998) "Adult neurogenesis: from canaries to the clinic." *Journal of Neurobiology*, 36(2): 267-86.

Herman et al. (1992) "Dopaminergic transplants in experimental parkinsonism: cellular mechanisms of graft-induced functional recovery." *Current Opinion in Neurobiology*, 2(5): 683-689.

Jin (2002) "Stem cell factor stimulates neurogenesis in vitro and vivo." *The Journal of Clinical Investigation*, 110(3): 311-319.

Kopen et al. "Marrow stromal cells migrate throughout forebrain and cerebellum, and they differentiate into astrocytes after injection into neonatal mouse brains." *Proceedings of the National Academy of Sciences U S A*, 96(19): 10711-10716, 1999.

Mezey et al. (2000 "Turning Blood into Brain: Cells Bearing Neuronal Antigens Generated in Vivo from Bone Marrow." *Science*, 290(5497): 1779-1782.

Sanchez-Ramos et al. (2000) "Adult Bone Marrow Stromal Cells Differentiate into Neural Cells in Vitro." *Experimental Neurology* 164(2): 247-256.

Wagner et al. (1999) "Stimulation of neonatal and adult brain neurogenesis by subcutaneous injection of basic fibroblast growth factor." *The Journal of Neuroscience*, 19(14): 6006-6016.

Watt and Hogan (2000) "Out of Eden: Stem Cells and Their Niches." *Science*, 287(5457): 1427-1430.

Woodbury et al. (2000) "Adult rat and human bone marrow stromal cells differentiate into neurons." *Journal of Neuroscience Research*, 61(4): 364-370.

Yazaki et al. (1994) "Differential expression patterns of mRNAs for members of the fibroblast growth factor receptor family, FGFR-1-FGFR-4, in rat brain." *Journal of Neuroscience Research*, 37(4): 445-452.

\* cited by examiner

*Primary Examiner*—Daniel C Gamett
(74) *Attorney, Agent, or Firm*—Weaver Austin Villeneuve & Sampson LLP; Tom Hunter

(57) ABSTRACT

This invention pertains to the identification of neurogenerative and/or neurotrophic factors that can induce migration of stem cells to neural tissue and/or induce proliferation and/or differentiation of such cells into neurons. Such agents include, but are not limited to stem cell factor (SCF), heparin binding EGF (HB-EGF), and VEGF.

13 Claims, 13 Drawing Sheets

NEUROGENERATIVE OR NEUROTROPHIC FACTORS FOR MITIGATING A SYMPTOM OF ISCHEMIA

CROSS-REFERENCE TO RELATED APPLICATIONS

This application claims priority to and benefit of U.S. Ser. No. 60/357,310, filed on Feb. 14, 2002, which is incorporated herein by reference in its entirety for all purposes.

STATEMENT AS TO RIGHTS TO INVENTIONS MADE UNDER FEDERALLY SPONSORED RESEARCH AND DEVELOPMENT

This work was supported by Grants from The National Institute of Neurological Disorders and Stroke, National Institutes of Health. The Government of the United States of America may have certain rights in this invention.

FIELD OF THE INVENTION

This invention pertains to the field of neurobiology. In particular this invention pertains to the identification of neurotrophic and neurogenerative factors that are of use in mitigating a symptom of ischemia. This invention also pertains to the discovery that cerebral neurogenesis can be induced by intranasal administration of growth factors.

BACKGROUND OF THE INVENTION

Stroke is the third most common cause of death in the United States. Despite progress in understanding molecular mechanisms of cell death after stroke, widely effective stroke treatment remains elusive. Recent studies on neurogenesis, the development of neurons from immature precursor cells, suggest that it might be possible for dead or injured neural cells to be replaced through this process. Support for this possibility includes evidence that neurogenesis continues to occur in the brains of adult mammals, including mice (Lim et al. (2000) *Neuron*, 28(3): 713-726; Yoshimura et al. (2001) *Proc Natl Acad Sci USA*, 98(10): 5874-5879), rats (Jin et al. (2001) *Proc Natl Acad Sci USA*, 98(8): 4710-4715; Liu et al. (1998) *J Neurosci*, 18(19): 7768-7778), non-human primates (McDermott et al. (1991) *J Anat*, 1991. 178: 45-63) and humans (Eriksson et al. (1998) *Nat Med*, 1998. 4(11): 1313-1317). Neural precursor cells include both self-renewing, totipotent "stem" cells and pluripotent "progenitor" cells, which can be isolated from adult brains and expanded in vitro (Fricker et al. (1999) *J Neurosci*, 1999. 19(14): 5990-6005; Gage et al. (1995) *Proc Natl Acad Sci USA*, 92(25): 11879-11883; Uchida et al. (2000) *Proc Natl Acad Sci USA*, 97(26): 14720-14725). These cells can subsequently be transplanted into the brain, where they are able to migrate extensively and to differentiate into neurons and glia (Suhonen et al. (1996) *Nature*, 1996. 383(6601): 624-627). This raises the intriguing possibility that neural precursor cells might be beneficial in the treatment of CNS diseases, including stroke.

Neural precursor cells transplanted into local regions of the brain can differentiate into neurons, and have the potential to improve symptoms in disorders like Parkinson's disease (Herman, et al. (1992) *Curr Opin Neurobiol*, 2(5): 683-689; Bjorklund (1992) *Curr Opin Neurobiol*, 2(5): 683-689; Gage (2000) *Science*, 287(5457): 1433-1438). However, there are several disadvantages of intracerebral neural precursor cell transplants. First, surgical transplantation may result in local tissue damage or stroke. Second, large numbers of neural precursors from fetal tissues are difficult to obtain. Third, the use of precursors from certain sources, such as human embryos, is ethically and politically controversial. Fourth, neural degeneration in some CNS diseases is extensive, multifocal or even global, which may require widespread replacement beyond the capabilities of surgical transplantation. Finally, intracerebral transplantation may be associated with adverse effects related to the unregulated function of ectopic tissue (Freed et al. (2001) *N Engl J Med*, 344(10): 710-719).

SUMMARY OF THE INVENTION

This invention pertains to the discovery that that (1) bone marrow-derived cells will migrate into the brain after systemic administration; (2) following focal cerebral ischemia, migrating marrow-derived cells will integrate appropriately into damaged brain regions and differentiate into functional neurons; (3) this process will result in partial recovery of brain function; and (4) the migration and differentiation of marrow-derived cells will be regulated by cellular and molecular mechanisms, including the secretion of soluble factors such as growth factors, and by the target tissue's microenvironment.

The invention thus provides methods of treating or mitigating ischemic-associated damage to neural cells or tissues where the methods involve systemically administering stem cells which can then migrate to the brain, and, particularly in the presence of one or more of the agents identified herein, proliferate and differentiate into nerves and other neural tissue.

Thus, in certain embodiments, this invention provides a method of inducing proliferation or differentiation of a neuron. The method typically involves contacting a neural cell with an agent selected from the group consisting of stem cell factor, heparin binding EGF (HB-EGF), fibroblast growth factor-2, and VEGF. The contacting can be by any of a variety of convenient methods including, but not limited to, introducing the agent factor directly into a mammalian brain, systemically administering the factor, administering the factor intranasally, and the like.

In another embodiment, this invention provides a method of mitigating neural damage associated with ischemia. This method typically involves administering to an organism (e.g. to a human or to a non-human mammal) a bone marrow stem cell (BMC). The bone marrow cell can, optionally, be administered on conjunction with a neurogenic or neurotrophic agent (e.g. stem cell factor (SCF), heparin binding EGBF (HB-EGF), FGF (e.g., FGF-2), and VEGF). The agent can be administered by any of a variety of convenient methods including, but not limited to, introducing the agent factor directly into a mammalian brain, systemically administering the factor, administering the factor intranasally, and the like.

In still another embodiment, this invention provides a method of inducing proliferation or differentiation of a neuron. The method typically involves contacting a neural cell with a component found in hypoxic conditioned medium (e.g. SCF).

This invention also provides a method of screening for an agent that mitigates neural damage associated with ischemia The method typically involves contacting a cell or a tissue with a test agent; and detecting a factor selected from the group consisting of stem cell factor, heparin binding EGF (HB-EGF), FGF-2, and VEGP, where an increase in expression or activity of the factor, as compared the expression or activity of the factor produced or secreted in a cell or tissue that is a negative control (e.g. a cell contacted with a lower concentration of the factor or not contacted with the factor)

indicates that the test agent is a good candidate for mitigating neural damage associated with ischemia. In certain embodiments, the cell or tissue is a neural cell or tissue.

In another embodiment, this invention provides a method of screening for an agent that mitigates neural damage associated with ischemia. The method typically involves contacting a cell or a tissue with a test agent; and detecting a morphological or physiological change in the cell or tissue that is characteristic of a response of the cell or tissue to hypoxia, where the response indicates that the test agent is a good candidate for mitigating neural damage associated with ischemia Also provided is a method of inducing neurogenesis in a mammal (e.g. a human or a non-human mammal). The method typically involves intranasally administering a neuroproliferative growth factor in a concentration sufficient to induce neuroproliferation in the mammal. Certain preferred factors include, but are not limited to fibroblast growth factor-2 (FGF-2), heparin-binding epidermal growth factor-like growth factor (HB-EGF), a fibroblast growth factor-2 (FGF-2) analogue, and a heparin-binding epidermal growth factor analogue. In certain embodiments, the growth factor is combined with a pharmaceutically acceptable excipient (e.g. an excipient for nasal administration). The growth factor can be formulated in a unit dosage formulation. In certain embodiments, the growth factor comprises a plurality of growth factors. In certain embodiments, the mammal is a mammal having or at risk for, or having, an acute or chronic neurodegenerative condition. In certain embodiments, the acute or chronic neurodegenerative condition is a condition selected from the group consisting of Alzheimer's disease, Parkinson's disease, spinal cord injury, cranial injury, physical trauma to the head or spinal cord; a brain concussion; ischemic stroke caused by thrombosis or embolism; cerebral hemorrhage, general circulatory failure, circulatory disruption caused by cardiac arrest, hemodynamic shock caused by loss of blood due to injury or hemorrhage elsewhere in the body; vasculatory damage caused by vascular disease, bacterial infection, viral infection, fungal infection, cerebral or spinal tumors, glial cell swelling, hypoxic injury to the brain caused by respiratory disruption, and post-operative brain injury or stress. In certain embodiments, the intranasal administration is within 1 week, more preferably within 24 hours of an acute neurological trauma.

In still yet another embodiment, this invention provides a method of mitigating one or more symptoms associated with acute or chronic neurodegenerative condition in a mammal (e.g. a human or non-human mammal). The method typically involves intranasally administering one or more neuroproliferative growth factors in a concentration sufficient to induce neuroproliferation in the mammal. Preferred growth factors include, but are not limited to, fibroblast growth factor-2 (FGF-2), heparin-binding epidermal growth factor-like growth factor (HB-EGF), a fibroblast growth factor-2 (FGF-2) analogue, a heparin-binding epidermal growth factor analogue, and the like. In certain embodiments, the growth factor is combined with a pharmaceutically acceptable excipient (e.g. an excipient for nasal administration). The growth factor can be formulated in a unit dosage formulation. In certain embodiments, the mammal is a mammal having or at risk for an acute or chronic neurodegenerative condition (e.g. Alzheimer's disease, Parkinson's disease, spinal cord injury, cranial injury, physical trauma to the head or spinal cord; a brain concussion; ischemic stroke caused by thrombosis or embolism; cerebral hemorrhage, general circulatory failure, circulatory disruption caused by cardiac arrest, hemodynamic shock caused by loss of blood due to injury or hemorrhage elsewhere in the body; vasculatory damage caused by vascular disease, bacterial infection, viral infection, fungal infection, cerebral or spinal tumors, glial cell swelling, hypoxic injury to the brain caused by respiratory disruption, and post-operative brain injury or stress, etc.). In certain embodiments, the intranasal administration is within 1 week, more preferably within 24 hours of an acute neurological trauma.

In certain embodiments, this invention provides pharmaceutical formulations. The formulations typically comprise one or more a neuroproliferative or neurotrophic factors; and a pharmaceutically compatible excipient (e.g. an excipient for nasal administration to a mammal). Certain factors include, but are not limited to fibroblast growth factor-2 (FGF-2), heparin-binding epidermal growth factor-like growth factor (HB-EGF), a fibroblast growth factor-2 (FGF-2) analogue, and a heparin-binding epidermal growth factor-like growth factor analogue. The factor(s) can be formulated in a unit dosage formulation.

This invention also provides a kit for mitigating one or more symptoms associated with ischemia or neural damage. The kit typically includes a container containing a pharmaceutical formulation comprising: a neuroproliferative growth factor; and a pharmaceutically compatible excipient for nasal administration to a mammal. In certain embodiments, the growth factor is selected from the group consisting of fibroblast growth factor-2 (FGF-2), heparin-binding epidermal growth factor-like growth factor (HB-EGF), a fibroblast growth factor-2 (FGF-2) analogue, a heparin-binding epidermal growth factor-like growth factor analogue. The growth factor can be formulated in a unit dosage formulation. In certain embodiments, the growth factor comprises a plurality of growth factors. In certain embodiments, the kit additionally includes instructional materials teaching intranasal administration of a neuroproliferative growth factor to induce neurogenesis in a mammal.

This invention also provides a method of screening for an agent that mitigates one or more symptoms associated with ischemia. The method typically involves contacting a cell with a test agent; and detecting a change in the expression level or activity of a neurogenic or neurotrophic factor (e.g. SCF, FGF, EGF, and HB-EGF, and the like) where an increase of expression level or activity of the neurogenic or neurotrophic factor as compared to the expression level of that factor in a negative control (e.g. a cell contacted with a lower concentration of the factor or a cell not contacted with the factor) indicates that the test agent is a good candidate for an agent that mitigates one or more symptoms associated with ischemia. The method can further involve recording test agents that alter expression or activity of the factor(s) in a database of modulators neural tissue repair. In certain embodiments, the expression level of the factor is detected by measuring the level of mRNA encoding the factor in the cell (e.g. by hybridizing the mRNA to a probe that specifically hybridizes to a mRNA encoding the factor). In certain embodiments, the hybridizing is according to a method selected from the group consisting of a Northern blot, a Southern blot using DNA derived from the RNA encoding the factor, an array hybridization, an affinity chromatography, and an in situ hybridization. In various embodiments, the probe is a member of a plurality of probes that forms an array of probes. In certain embodiments, the level of mRNA encoding the factor is measured using a nucleic acid amplification reaction. In certain embodiments, the level of the factor is detected by determining the protein expression level of the factor in the biological sample (e.g. via a method selected from the group consisting of capillary electrophoresis, a Western blot, mass spectroscopy, ELISA, immunochromatography, and immunohistochemistry, and the like). In certain embodiments, the cell is cultured ex vivo. In certain embodiments, the test agent is not an antibody, and/or not a protein, and/or not a nucleic acid. In certain embodiments, the test agent is a small organic molecule.

This invention also provides a method of prescreening for an agent that mitigates one or more symptoms associated with ischemia and/or that induces neural repair or differentiation. The method typically involves contacting a neurogenic or neurotrophic factor (e.g. SCF, FGF, EGF, and HB-EGF), or a nucleic acid encoding the factor with a test agent; and detecting specific binding of the test agent to the factor or to the nucleic acid, where the specific binding indicates that the test agent is a potential agent that mitigates one or more symptoms associated with ischemia. The method can further involve recording test agents that specifically bind to the factor or to the nucleic acid in a database of candidate modulators of neural repair. In certain embodiments, the test agent is not an antibody, and/or not a protein, and/or not a nucleic acid. The detecting can comprise detecting specific binding of the test agent to the nucleic acid (e.g. via Northern blot, a Southern blot using DNA, an array hybridization, an affinity chromatography, in situ hybridization, etc.). In certain embodiments, the detecting comprises detecting specific binding of the test agent to the factor (e.g., via a method selected from the group consisting of capillary electrophoresis, a Western blot, mass spectroscopy, ELISA, immunochromatography, immunohistochemistry, etc.). In certain embodiments, the test agent is contacted directly to the factor or to the nucleic acid encoding the factor. In certain embodiments, the test agent is contacted to a cell containing the factor or the nucleic acid encoding the factor. The cell can be a cell cultured ex vivo. In certain embodiments, the test agent is contacted to an animal comprising a cell containing the factor or the nucleic acid encoding the factor.

Definitions

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

The term "neurotrophic and/or neurogenerative" factor refers to an agent that induces migration of a cell to a neural tissue (neurotrophic) and/or that induces growth or differentiation of a neural cell or tissue.

The term "antibody", as used herein, includes various forms of modified or altered antibodies, such as an intact immunoglobulin, an Fv fragment containing only the light and heavy chain variable regions, an Fv fragment linked by a disulfide bond (Brinkmann et al. (1993) *Proc. Natl. Acad. Sci. USA*, 90: 547-551), an Fab or (Fab)'2 fragment containing the variable regions and parts of the constant regions, a single-chain antibody and the like (Bird et al. (1988) *Science* 242: 424-426; Huston et al. (1988) *Proc. Nat. Acad. Sci. USA* 85: 5879-5883). The antibody may be of animal (especially mouse or rat) or human origin or may be chimeric (Morrison et al. (1984) *Proc Nat. Acad. Sci. USA* 81: 6851-6855) or humanized (Jones et al. (1986) *Nature* 321: 522-525, and published UK patent application #8707252).

The terms "binding partner", or "capture agent", or a member of a "binding pair" refers to molecules that specifically bind other molecules to form a binding complex such as antibody-antigen, lectin-carbohydrate, nucleic acid-nucleic acid, biotin-avidin, etc.

The term "specifically binds", as used herein, when referring to a biomolecule (e.g., protein, nucleic acid, antibody, etc.), refers to a binding reaction which is determinative of the presence biomolecule in heterogeneous population of molecules (e.g., proteins and other biologics). Thus, under designated conditions (e.g. immunoassay conditions in the case of an antibody or stringent hybridization conditions in the case of a nucleic acid), the specified ligand or antibody binds to its particular "target" molecule and does not bind in a significant amount to other molecules present in the sample.

The terms "nucleic acid" or "oligonucleotide" or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) *Tetrahedron* 49(10):1925) and references therein; Letsinger (1970) *J. Org. Chem.* 35:3800; Sprinzl et al. (1977) *Eur. J. Biochem.* 81: 579; Letsinger et al. (1986) *Nucl. Acids Res.* 14: 3487; Sawai et al. (1984) *Chem. Lett.* 805, Letsinger et al. (1988) *J. Am. Chem. Soc.* 110: 4470; and Pauwels et al. (1986) *Chemica Scripta* 26: 1419), phosphorothioate (Mag et al. (1991) *Nucleic Acids Res.* 19:1437; and U.S. Pat. No. 5,644, 048), phosphorodithioate (Briu et al. (1989) *J. Am. Chem. Soc.* 111 :2321, O-methylphophoroamidite linkages (see Eckstein, *Oligonucleotides and Analogues: A Practical Approach*, Oxford University Press), and peptide nucleic acid backbones and linkages (see Egholm (1992) *J. Am. Chem. Soc.* 114:1895; Meier et al. (1992) *Chem. Int. Ed. Engl.* 31: 1008; Nielsen (1993) *Nature*, 365: 566; Carlsson et al. (1996) *Nature* 380: 207). Other analog nucleic acids include those with positive backbones (Denpcy et al. (1995) *Proc. Natl. Acad Sci. USA* 92: 6097; non-ionic backbones (U.S. Pat. Nos. 5,386,023, 5,637,684, 5,602,240, 5,216,141 and 4,469,863; Angew. (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghui and P. Dan Cook; Mesmaeker et al. (1994), *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, ASC Symposium Series 580, *Carbohydrate Modifications in Antisense Research*, Ed. Y. S. Sanghui and P. Dan Cook Nucleic acids containing one or more carbocyclic sugars are also included within the definition of nucleic acids (see Jenkins et al. (1995), *Chem. Soc. Rev.* pp 169-176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions. The term "stringent conditions" refers to conditions under which a probe will hybridize preferentially to its target subsequence, and to a lesser extent to, or not at all to, other sequences. Stringent hybridization and stringent hybridization wash conditions in the context of nucleic acid hybridization are sequence dependent, and are different under different environmental parameters.

An extensive guide to the hybridization of nucleic acids is found in, e.g., Tijssen (1993) *Laboratory Techniques in Biochemistry and Molecular Biology—Hybridization with Nucleic Acid Probes part I, chapt 2, Overview of principles of hybridization and the strategy of nucleic acid probe assays*, Elsevier, N.Y. (Tijssen). Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on an array or on a filter in a Southern or northern blot is 42° C. using standard hybridization solutions (see, e.g., Sambrook (1989) *Molecular Cloning: A Laboratory Manual* (2nd ed.) Vol. 1-3, Cold Spring Harbor Laboratory, Cold Spring Harbor Press, NY, and detailed discussion, below), with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, e.g., Sambrook supra.) for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example of a low stringency wash for a duplex of, e.g., more than 100 nucleotides, is 4× to 6×SSC at 40° C. for 15 minutes.

The term "test agent" refers to an agent that is to be screened in one or more of the assays described herein. The agent can be virtually any chemical compound. It can exist as a single isolated compound or can be a member of a chemical (e.g. combinatorial) library. In a particularly preferred embodiment, the test agent will be a small organic molecule.

The term "small organic molecule" refers to a molecule of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

The term database refers to a means for recording and retrieving information. In preferred embodiments the database also provides means for sorting and/or searching the stored information. The database can comprise any convenient media including, but not limited to, paper systems, card systems, mechanical systems, electronic systems, optical systems, magnetic systems or combinations thereof. Preferred databases include electronic (e.g. computer-based) databases. Computer systems for use in storage and manipulation of databases are well known to those of skill in the art and include, but are not limited to "personal computer systems", mainframe systems, distributed nodes on an inter- or intranet, data or databases stored in specialized hardware (e.g. in microchips), and the like.

The following abbreviations are used herein: subventricular zone (SVZ); subgranular zone (SGZ); dentate gyrus (DG); brain-derived neurotrophic factor (BDNF); middle cerebral artery (MCA); bromodeoxyuridine (BrdU); proliferating cell nuclear antigen (PCNA); stem cell factor (SCF); DNA polymerase I-mediated biotin-dATP nick translation (PANT); neuronal nuclear antigen (NeuN); microtubule-associated protein-2 (MAP-2); glial fibrillary acidic protein (GFAP); embryonic nerve cell adhesion molecule (E-NCAM); 4□□, 6-diamidine-2-phenylindole dihydrochloride (DAPI); humanized *Renilla reniformis* green fluorescent protein (hrGFP); 3-(4,5-dimethylthiazol-2-yl)-2,5-diphenyl tetrazolium bromide (MTT); artificial cerebrospinal fluid (aCSF); hypoxia-conditioned medium (HCM).

BRIEF DESCRIPTION OF THE DRAWINGS

(FIG. 8C). *, $P<0.05$ compared to Control (t-test).

DETAILED DESCRIPTION

Figure 1:
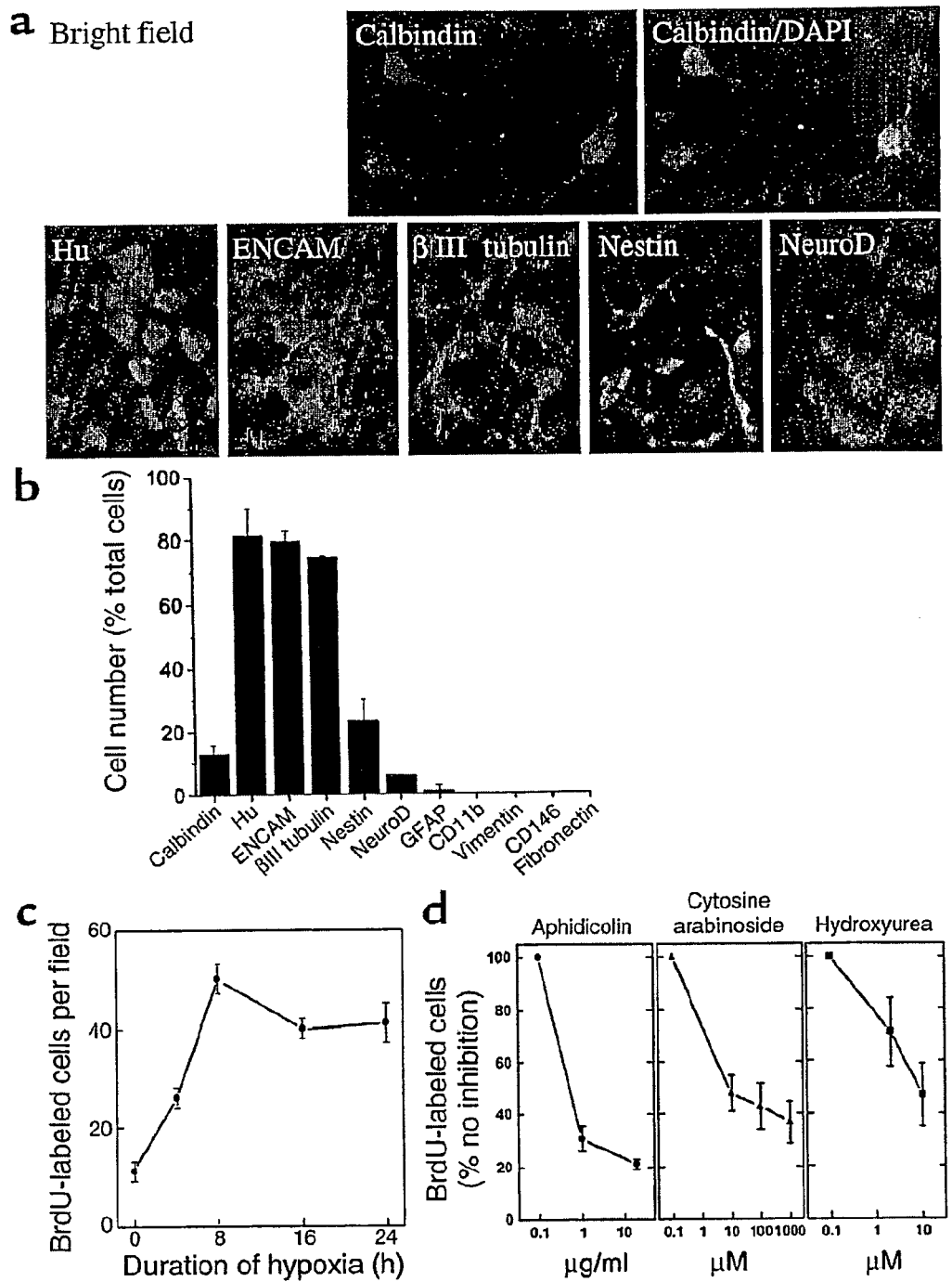
FIG. 1 shows that hypoxia increases BrdU incorporation in cerebral cortical cultures. (Panel a) Cortical cultures were stained with Ab's against the indicated markers and counterstained with the nuclear stain DAPI (blue). (Panel b) The percentage of cells expressing each marker is shown, indicating that most cells at this stage in culture are immature neurons. (Panel c) Cultures were treated with BrdU and deprived of oxygen for up to 24 hours, and BrdU was visualized by immunocytochemistry and quantified by cell counting. (Panel d) The hypoxia-induced increase in BrdU incorporation was reduced by the cell cycle inhibitors aphidicolin, cytosine arabinoside, and hydroxyurea. Data shown are representative fields (Panel a) or mean±SEM, n=3(b-d).

This invention pertains to the discovery that that (1) bone marrow-derived cells will migrate into the brain after systemic administration; (2) following focal cerebral ischemia, migrating marrow-derived cells will integrate appropriately into damaged brain regions and differentiate into functional neurons; (3) this process will result in partial recovery of brain function; and (4) the migration and differentiation of marrow-derived cells will be regulated by cellular and molecular mechanisms, including the secretion of soluble factors such as growth factors, and by the target tissue's microenvironment.

The invention thus provides methods of treating or mitigating ischemic-associated damage to neural cells or tissues where the methods involve systemically administering stem cells which can then migrate to the brain, and, particularly in the presence of one or more of the agents identified herein, proliferate and differentiate into nerves and other neural tissue.

In certain embodiments, this invention pertains to the identification of neurogenerative and/or neurotrophic factors that can induce migration of stem cells to neural tissue and/or induce proliferation and/or differentiation of such cells into neurons. The factors can be used to induce proliferation of neural tissue in organisms (e.g. mammals) suffering neural damage characteristic of ischemia.

It was also a discovery of this invention that factors associated (e.g. expressed and/or secreted, etc.) in hypoxic tissues, especially hypoxic neural tissues can induce proliferation and/or differentiation of neural tissue. These factors, found in hypoxic conditioned media, include, but are not limited to stem cell factor, heparin binding EGF (HB-EGF), FGF-2, and VEGF.

The factors can be administered to an organism (e.g. a human or non-human mammal) prophylactically or therapeutically. In certain embodiments, rather than administering the factors, agent can be administered that increase expression or activity of the neurogenerative and/or neurotrophic factors. Such agents can readily be identified by screening systems such as those described herein.

Thus, in certain embodiments, this invention provides methods of screening for agents that mitigate one or more symptoms of ischemic injury to neural tissue and/or that induce neuroregeneration. The methods involve contacting a cell tissue or organism with a test agent and measuring the ability of that agent to increase expression or activity of a neurogenerative and/or neurotrophic factor as described herein.

I. Methods of Inducing Proliferation or Differentiation of a Neuron or a Neural Tissue and/or Mitigating a Symptom of Ischemia In certain embodiments, this invention provides methods of mitigating one or more symptoms associated with ischemia. A variety of conditions can give rise to such injury. Such conditions include, but are not limited to spinal cord injury, cranial injury, physical trauma to the head or spinal cord; a brain concussion; ischemic stroke caused by thrombosis or embolism; cerebral hemorrhage, general circulatory failure, circulatory disruption caused by cardiac arrest, hemodynamic shock caused by loss of blood due to injury or hemorrhage elsewhere in the body; vasculatory damage caused by vascular disease, bacterial infection, viral infection, fungal infection, cerebral or spinal tumors, glial cell swelling, hypoxic injury to the brain caused by respiratory disruption, and post-operative brain injury or stress.

In certain embodiments, the methods involve contacting a neural cell or tissue with one or more of the neurotrophic or neurogenerative factors described herein (e.g. FGF-2, HB-EGF, SCF, etc.). In certain embodiments, this involves administering to an organism in need thereof (e.g., therapeutically and/or prophylactically) one or more of the the neurotrophic or neurogenerative factors described herein, preferably in a dosage sufficient to induce a neurotrophic response (e.g. migration of progenitor cells to the site of injury) and/or to induce regeneration/differentiation of neural cells or tissues.

Similarly, in certain embodiments, this invention provides a method of inducing proliferation or differentiation of a neuron and/or a neural tissue. The method involves contacting a neural cell or tissue with one or more factor(s) selected from the group consisting of stem cell factor (SCF), heparin binding EGF (HB-EGF), fibroblast growth factor-2, and VEGF.

Other neurogenerative and/or neurotrophic factors can be used in the methods of this invention. Such factors include, but are not limited to epithelial growth factor (EGF), the FGF factors (e.g. FGF-2), brain-derived neurotrophic factor (BDNF) (Zigova et al. (1998) *Mol Cell Neurosci*, 11(4): 234-245) insulin-like growth factor-1 (IGF-1), glutamate, NMDA receptor antagonists, and the like.

Contacting of the nerve cell or tissue with the desired factor(s) can be accomplished by a number of methods including, but not limited to direct introduction into the subject's brain (e.g. during a surgical procedure, via a cannula, etc.), treatment of the subject with one or more drugs that induce proliferation of the factor (e.g. one or more drugs identified by the screening methods described herein), or the factor(s) can be administered systemically, alone, or in conjunction with stem cell(s) (e.g. BMCs). It was also a surprising discovery of this invention that various growth factors (e.g. FGF-2, and HB-EGF) are effective at inducing cerebral neurogenesis when introduced by intranasal administration.

In certain other embodiments this invention provides a method of mitigating neural damage associated with ischemia. The methods typically involve administering to an organism a bone marrow stem cell, HSC, MSC, etc. The cell can be administered in conjunction with a neurogenerative and/or neurotrophic factor selected from the group consisting of stem cell factor, heparin binding EGF (HB-EGF), FGF-2, and VEGF.

A) Administration of Agents to Stimulate Neurogenesis

The neurotrophic and/or neurogenerative factors (e.g., stem cell factor (SCF), heparin binding EGF (HB-EGF), fibroblast growth factor-2, VEGF, or biologically active fragments thereof) of this invention are useful for intravenous, parenteral, topical, oral, or local administration (e.g., by aerosol or transdermally). Particularly preferred modes of administration include intra-arterial injection, intravenous injection, direct administration into neural tissue (e.g. during a surgical procedure or via cannulae, etc.), or delivery in a biodegradable matrix. In certain embodiments, the factor(s) are typically combined with a pharmaceutically acceptable carrier (excipient) to form a pharmacological composition. Pharmaceutically acceptable carriers can contain a physiologically acceptable compound that acts, for example, to stabilize the composition or to increase or decrease the absorption of the agent. Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of the anti-mitotic agents, or excipients or other stabilizers and/or buffers.

Other physiologically acceptable compounds include wetting agents, emulsifying agents, dispersing agents or preservatives which are particularly useful for preventing the growth or action of microorganisms. Various preservatives are well known and include, for example, phenol and ascorbic acid. One skilled in the art would appreciate that the choice of a pharmaceutically acceptable carrier, including a physiologically acceptable compound depends, for example, on the rout of administration of the anti-mitotic agent and on the particular physiochemical characteristics of the anti-mitotic agent. Illustrative formulations for the delivery of proteins known to those of skill in the art (see, e.g., the ProLease® biodegradable microsphere delivery system for proteins and peptides (Tracy (1998) *Biotechnol. Prog.* 14: 108; Johnson et al. (1996), *Nature Med.* 2: 795; Herbert et al. (1998), *Pharmaceut. Res.* 15, 357).

The pharmaceutical compositions can be administered in a variety of unit dosage forms depending upon the method of administration. For example, unit dosage forms suitable for oral administration include powder, tablets, pills, capsules and lozenges. It is recognized that the protein(s), if administered orally, are preferably protected from digestion. This is typically accomplished either by complexing the protein with a composition to render it resistant to acidic and enzymatic hydrolysis or by packaging the protein in an appropriately resistant carrier such as a liposome. Means of protecting compounds from digestion are well known in the art (see, e.g., U.S. Pat. No. 5,391,377 describing lipid compositions for oral delivery of therapeutic agents).

The pharmaceutical compositions of this invention will commonly comprise a solution of the neurotrophic/neurogenerative factor(s) dissolved in a pharmaceutically acceptable carrier, preferably an aqueous carrier for water-soluble proteins. A variety of carriers can be used, e.g., buffered saline and the like. These solutions are sterile and generally free of undesirable matter. These compositions may be sterilized by conventional, well known sterilization techniques. The compositions can contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

The concentration of neurotrophic/neurogenerative factor(s) in these formulations can vary widely, and will be selected primarily based on fluid volumes, viscosities, body weight and the like in accordance with the particular mode of administration selected and the patient's needs. Typically the neurotrophic/neurogenerative factor(s) are utilized in the form of a pharmaceutically acceptable solution (including reconstitution from a lyophilized form). In certain embodiments, it is desirable to solubilize the neurotrophic/neurogenerative factor(s) at concentrations of at least about 1 mg/ml, preferably about 2 to 8 mg/ml, so that a pharmaceutically effective amount of protein can be delivered without undue volumes of carrier being necessary. For some applications, concentrations above 2 mg/ml may be desirable.

It was a surprising discovery of this invention that certain factors (e.g., SCF, FGF-2, etc.), when administered intranasally can induce neurogenesis (see, e.g., Example 3).

Thus, in certain embodiments, this invention contemplates the use of inhalation administration of neurogenerative and/or neurotrophic factors, particularly via inhalators, such as for dry powders or aerosols. As with skin drug administration, inhalation drug administration provides a means of bypassing the gastrointestinal portal vein entry first-pass metabolism and as well provides a means of rapid access to the general circulation.

Drugs delivered from inhalators are typically airborne fine particles. The particles can be aerosolized suspensions (e.g., admixed with a propellant gas, i.e., a chlorofluorocarbon) and/or can be dispersed powders (generally admixed with an excipient). These particles can be either liquids or solids.

The size of the airborne particles can be important. Particles larger than about 10 micrometers diameter are unlikely to reach the lungs for deposit. Conversely, particles smaller than about 0.5 micrometers diameter can be exhaled again.

One of the problems with inhalation delivery is that only approximately 10-20% of the drug is delivered to the lung alveoli. The rest is deposited into the oro-pharynx. If this were swallowed, it would go into a gastrointestinal absorption portal vein liver entry and metabolism pathway. Thus, mouth rinsing is frequently recommended.

Where the airborne drug being inhaled is in a fine particle form with the appropriate formulation, it is rapidly absorbed in the oral cavity if swallowing is delayed as it will with sublingual administration. Thus, inhalation administration presents a combined buccalingual pathway (as well as an oropharyngeal pathway) plus the lung absorption means of bypassing the gastrointestinal liver first-pass metabolism.

There are several inhalator delivery known to those of skill in the art. One is a traditional nebulizer that works via a mechanism similar to the familiar perfume atomizer. The airborne particles are generated by a jet of air from either a compressor or compressed gas cylinder passing through the device. Newer nebulizers often utilize an ultrasonic nebulizer by vibrating the liquid at speeds, e.g., of up to about 1 MHZ.

Another type of inhalator delivery system is the metered dose inhaler (MDI). This has been widely used because of its convenience and usually contains a suspension of the drug in a aerosol propellant.

The typical dry powder inhaler has the appropriate dose often placed in a capsule along with a flow aid or filler excipient, such as large lactose or glucose particles. Inside the device, the capsule is initially either pierced by needles (SPINHALER®) or sheered in half (ROTOHALER®). Propellers turning cause the capsule contents to enter the air stream and to be broken up into small particles (see also, DISKHALER®, TURBUHALER®, plus numerous other dry powder inhalation delivery devices). For a review, see Taburet and Schmit (1994) *Clin. Pharmacokinet.*, 26(5):396-418.

More recently, Inhale Therapeutic Systems has created an inhalator delivery system that integrates customized formulation and proprietary fine powder processing and packaging technologies with their proprietary inhalation device for efficient reproducible deep-lung delivery. Their process of providing agglomerate composition compounds of units of aggregated fine particles and methods for manufacture and use of the units has recently been covered by a series of patents. The particle size containing the drug is in the optimum range for deep-lung delivery and has a suitable friability range. The Inhale delivery systems are described, in U.S. Pat. Nos. 5,458,135, 5,607,915, 5,654,007, and 5,655,516.

Other variations of pulmonary inhalation of drugs via an inhalator delivery system include the use of liposomes (microscopic phospholipid vesicles). The liposomal delivery of drugs slows the uptake of drug absorption from the lungs thus, providing a sustained drug release (see, e.g., Hung et al. (1995) *Anesthesiol.*, 82:277-284).

General background information with respect to dry powder inhalers can be seen in U.S. Pat. Nos. 2,642,063, 3,807, 400, 3,906,950, 3,991,761, 3,992,144, 4,013,075, 4,371,101, 4,601,897, 4,841,964, 4,955,945, 5,173,298, 5,369,117, 5,388,572, 5,388,573, 5,394,869, 5,415,162, 5,503,869 and in PCT Publications: WO 92/00115, WO 94/20164, WO 93/24166, and the like The dosage regimen will be determined by the clinical indication being addressed, as well as by various patient variables (e.g. weight, age, sex) and clinical presentation (e.g. extent of injury, site of injury, etc.). In general, the dosage of neurotrophic/neurogenerative factor(s) will be in the range of from 1 to about 10000 µg/kg, preferably from about 10 to 1000 µg/kg, more preferably from about 10 to 100 µg/kg.

B) Administration of Stem Cells to Stimulate Neurogenesis and Repair

In certain embodiments, this invention contemplates the use of progenitor or stem cells alone, or in combination with a neurogenerative/neurotrophic factor to stimulate neurogenesis and repair, particularly in the treatment or mitigation of symptoms associated with ischemia. In certain embodiments, the use of neural stem cells or progenitor cells is contemplated. In was a surprising discovery of this invention, however, that bone marrow-derived cells will migrate into the brain after systemic administration, that following focal cerebral ischemia, migrating marrow-derived cells will integrate appropriately into damaged brain regions and differentiate into functional neurons; that this process can result in recovery of brain function. Thus, certain embodiments contemplate the local or system ic administration of bone marrow cells to effect neural regeneration or repair.

1) Neural Stem Cells: Definition and Location in Adult Brain

It has been thought for some time that the brains of adult mammals do not generate new nerve cells, although Altman first observed the proliferative potential of adult rodent brain in the 1960s (Altman et al. (1995) *J Comp Neurol,* 124: 319-336; Altman (1962) *Science,* 135: 1127-1128). After several years of debate, it is now accepted that the rostral subventricular zone (SVZ) surrounding the lateral ventricles and the subgranular zone (SGZ) of the hippocampal dentate gyrus are active proliferative regions that generate neurons (Chiasson et al. (1999) *J Neurosci,* 19(11): 4462-4471), astrocytes (Doetsch et al. (1999) *Cell,* 97(6): 703-716) and oligodendrocytes (Chiasson et al. (1999) *J Neurosci,* 19(11): 4462-4471; Johansson et al. (1999) *Cell,* 96(1): 25-34) continuously throughout life in mice (Yoshimura et al. (2001) *Proc Natl Acad Sci USA,* 98(10): 5874-5879), rats (Jin et al. (2001) *Proc Natl Acad Sci USA,* 98(8): 4710-4715), non-human primates (McDermott et al. (1991) *J Anat,* 1991. 178: 45-63) and humans (Eriksson et al. (1998) *Nat Med,* 1998. 4(11): 1313-1317). According to terminology adopted from hematopoiesis, neural precursor cells are often classified as stem cells (defined as self-renewing, totipotent precursors), progenitor cells (which arise from stem cells and are not self-renewing, but which can give rise to multiple cell types such as neurons and astrocytes), and committed precursors (which give rise to only a single cell type, such as neurons, but are not yet functionally mature) (Gage (2000) *Science,* 287(5457): 1433-1438). In this application, however, the terms stem cell, progenitor and precursor will be used interchangeably unless stated otherwise.

Dividing stem cells give rise to progenitors that migrate to regions of differentiation. As the progenitor migrates, it matures further until it reaches a site where it stops and either becomes quiescent or fully differentiates into a functional cell. Certain phenotypic markers can discriminate between different cell types or different maturational states of the same cell. These include neuronal nuclear antigen (NeuN) (Lois and Alvarez-Buylla (1994) *Science,* 264(5162): 1145-1148) and microtubule-associated protein-2 (MAP2) (Kaneko et al. (2000) *Dev Neurosci,* 22(1-7): 139-153), which identify mature neurons, glial fibrillary acid protein (GFAP) for astrocytes (Francis et al. (1999) *Neuron,* 23(2): 247-256), and galactocerebroside (GalC) for oligodendro-cytes (des Portes et al. (1998) *Hum Mol Genet,* 7(7): 1063-1070). The doublecortin (DCX) gene. Phenotype markers in the pathways of neural differentiation (Kaneko et al. (2000) *Dev Neurosci,* 22(1-7): 139-153) encodes isoforms of a highly hydrophilic protein that is highly expressed in migrating and differentiating neurons in fetal and adult brain (Francis et al. (1999) *Neuron,* 23(2): 247-256; des Portes et al. (1998) *Hum Mol Genet,* 7(7): 1063-1070). A highly polysialylated form of neural cell adhesion molecule (PSA-NCAM) is expressed on migrating cells in the RMS and SGZ (Bonfanti et al. (19940 *Neuroscience,* 62(1): 291-305). As SGZ cells mature into granule cells and stop migrating, they no longer express PSA-NCAM, which may be involved in cell migration (Rousselot et al. (1995) *J Comp Neurol,* 351(1): 51-61; Alonso et al. (1999) *J Comp Neurol,* 405(4): 508-528). Immature neurons can also identified using markers including Nestin, a protein expressed by neuronal stem cells (Kaneko et al. (2000) *Dev Neurosci,* 22(1-7): 139-153), αIII tubulin, an earlier marker than TuJ-1 for the neuronal lineage in vivo (Panarraga et al. (1999) *Eur J Neurosci,* 11(2): 516-527), and Hu, a neuron-specific RNA-binding protein that begins to be expressed in neuronal nuclei and somata soon after differentiation (Marusich et al. (1994) *J Neurobiol,* 25(2): 143-155). Musashi 1 is another RNA-binding protein, expressed in stem cells, which is limited to the SVZ in the adult brain (Kaneko et al. (2000) *Dev Neurosci,* 22(1-7): 139-153). Therefore, the expression of specific proteins can define the serial stages in neuronal precursor ontogeny.

Isolation and culture of neural precursors from adult brain is readily accomplished. Under certain conditions, neural precursor cells from adult rodent and human brain can grow either in monolayers on tissue culture plates (McKay (1997) *Science,* 276(5309): 66-71; Ray et al. (1993) *Proc Natl Acad Sci USA,* 90(8): 3602-3606) or as self-adherent complexes of cells that form clusters called neurospheres (Reynolds et al. (1992) *J Neurosci,* 12(11): 4565-4574); both can differentiate into neurons, astrocytes, and oligodendrocytes in predictable proportions (McKay (1997) *Science,* 276(5309): 66-71; Johe et al. (1996) *Genes Dev,* 10(24): 3129-3140). For example, single cells isolated from the adult mouse brain can proliferate in response to basic FGF (FGF-2) or epidermal growth factor (EGF) to form neurospheres that generate more spheres and give rise to glia and neurons (Richards et al. (1992) *J Neurosci Res,* 33(3): 476-484). Rodent (Lois and Alvarez-Buylla (1994) *Science,* 264(5162): 1145-1148) and human (Fricker et al. (1999) *J Neurosci,* 1999. 19(14): 5990-6005) neurospheres in long-term culture generate new neurons when transplanted into the DG granule cell zone and generate olfactory neurons when transplanted into the RMS. These neurons express neurotransmitter phenotypes, such as tyrosine hydroxylase (Gage et al. (1995) *Proc Natl Acad Sci USA,* 92(25): 11879-11883; Suhonen et al. (1996) *Nature,* 383(6601): 624-627), suggesting that the neural cultures support the growth of precursor cells capable of differentiation as well as engraftment. Interestingly, these cells do not generate neurons when implanted into regions that do not normally give rise to new neurons in the adult, such as the cerebellum and striatum, suggesting that the local microenvironment is important in regulating proliferation, differentiation, or migration of adult neural precursor cells (Brustle et al. (1997) *Proc Natl Acad Sci USA,* 94(26): 14809-14814). Moreover, neurospheres from adult brain transplanted to an irradiated host mouse can also generate blood cell lineages, including myeloid, lymphoid and more primitive hematopoietic cells (Gould et al. (1999) *Science,* 286(5439): 548-552), suggesting that the potential of neuronal stem cells may not only extend beyond the brain region from which they arise, but may not be restricted to the brain at all.

Neural stem cells in the SVZ of adult brain can be identified by stable S-phase markers such as $^3$H-thymidine and BrdU (Altman and Das (1965) *J Comp Neurol,* 124: 319-336), by expression of immature neuronal marker Nestin (Reynolds and Weiss (1992) *Science* 255(5052): 1707-1710), and by their ability to form neurospheres that give rise to multiple cell types in vitro (Craig et al. (1996) *J Neurosci,* 16(8): 2649-2658). Four cell types have been identified in adult SVZ by ultrastructural and immunocytochemical studies: (1) neuroblasts, or Type A cells (dark cells); (2) astrocytes, or Type B1 and B2 cells (light cells); (3) undifferentiated, or Type C cells, which may correspond to neuronal precursors, but which are not found in the rostral migratory stream (RMS) (Doetsch et al. (1997) *J Neurosci,* 17(13): 5046-5061); and (4) ependymal cells (Doetsch et al. (1999) *Cell,* 97(6): 703-716; Johansson et al. (1999) *Cell,* 96(1): 25-34). The fate of stem cells in the SVZ remains unclear: some may migrate into the olfactory bulb (OB) via the RMS and differentiate, whereas others may die shortly after their genesis. The SGZ, a thin lamina between the hilar region and the granule cell layer of the hippocampal dentate gyrus (DG), retains the potential to form new neurons into adulthood (Gage, et al.

(1998) *J Neurobiol*, 36(2): 249-266). In rodents, the rate of neurogenesis declines with age (Kuhn et al. (1996) *J Neurosci*, 16(6): 2027-2033), but the number of granule cells in DG increases into midlife and reaches a plateau thereafter (Kempermann et al. (1998) *J Neurosci*, 18(9): 3206-3212). Neurogenesis persists in the DG in elderly rodents (Gould et al. (1999) *Proc Natl Acad Sci USA*, 96(9): 5263-5267) and humans (Kukekov et al. (1999) *Exp Neurol*, 156(2): 333-344) to maintain an equilibrium between production of newborn cells and neuronal loss. Although evidence of increased cell death in the dentate has been suggested, the exact relationship between the birth of new neurons and the death of older ones remains unclear.

Migration is one fate of stem cells that arise in SVZ and SGZ. Stem cells in the SVZ generate immature neurons that aggregate to form an extensive network of neuroblast chains along the lateral wall of the lateral cerebral ventricle (Doetsch, and Alvarez-Buylla (1996) *Proc Natl Acad Sci USA*, 93(25): 14895-14900). These chains of neuroblasts form a highly restricted migratory route, the RMS, which extends from the anterior SVZ into the OB. Unlike the radial glial-guided migration of young neurons during early brain development (Rakic (1990) *Experientia*, 46(9): 882-891), neuroblasts undergoing "chain migration" in the adult SVZ/RMS migrate along one another, which involves interactions between the migrating cells and tube-like structures formed by specialized astrocytes (Lois et al. (1996) *Science*, 271 (5251): 978-981). Neuroblasts migrate rostrally within the RMS to enter the OB, whereupon they differentiate into local interneurons (Luskin (1993) *Neuron*, 11(1): 173-189). However, the OB is not essential for proliferation and directed migration of SVZ precursors, since the proportion of dividing or dying cells in the RMS was not significantly affected after bulbectomy (Kirschenbaum et al. (1999) *J Neurosci*, 19(6): 2171-2180).

2. Neurogenesis from Marrow-derived Cells

Two types of stem cells are found in the bone marrow. One is hematopoietic stem cells (HSC), which can differentiate into all types of blood cells, and another is non-hematopoietic stem cells or bone marrow stromal cells (MSC) (also referred as colony-forming-unit fibroblasts or mesanchymal stem cells), which are progenitors of skeletal tissue components such as bone, cartilage, hematopoietesis-supporting stroma and adipocytes (Prockop (1997) *Science*, 276(5309): 71-74). In this application, the term "BMC" will be used when a combined population of both HSC and MSC is being referred to and/or when homogeneous populations of HSC and MSCs are being referred to.

Approximately 0.05% to 0.5% of the total number of the marrow cells are HSC and ~0.125% are stromal cells in the human and mouse (Morrison et al. (1995) *Annu Rev Cell Dev Biol*, 11: 35-71; Nardi and Alfonso (1999) *Braz J Med Biol Res*, 32(5): 601-609), and both can differentiate into neural cells. It is well known that such cells are capable of replenishing tissues in which they reside, such as blood, muscle, liver, and skin. However, recent studies show that adult stem cells are not restricted to their tissues of origin, but can trans-differentiate or be reprogrammed to express genes typical of different cell types. MSC of mouse, rat, and human can differentiate into cells with features of a neuronal or astrocytic phenotype under certain culture conditions, such as in the presence of BDNF and EGF.

When transplanted into SVZ and SGZ of the adult rat brain, MSC migrated specifically along the RMS, and exhibited site-specific neuronal differentiation in the granular and periglomerular layers of the OB and in the dentate granule cell layer. MSC in the striatum or hippocampus can differentiate into mature astrocytes or microglia. The capability of bone marrow-derived cells to generate neuron-like cells is further evidenced in vivo. After intravascular delivery of BMC from adult mice that express GFP into lethally irradiated adult hosts, BMC migrated into several regions of the brain, including the OB, cortex, hippocampus, and cerebellum. These BMC expressed gene products typical of neurons, and were able to activate the transcription factor, cAMP response element-binding protein (CREB), in a manner that suggested they were responding to their environment like native neurons. When BMC from adult male mice were injected via intraperitoneal into newborn female mice incapable of developing cells of the myeloid and lymphoid lineages, the Y chromosome-positive cells migrated into several brain regions, including cortex, hypothalamus and striatum, where they expressed neuron-specific antigens. The route of entry of BMC into the CNS is unknown, but may be primarily via the cerebrospinal fluid.

3) Modes of Administration

Methods of isolating and administering progenitor or stem cells are well known to those of skill in the art. Using, e.g. the markers described herein, neural progenitor cells can readily be identified and/or isolated (see, e.g., examples).

In protocols typical for infusion or re-infusion of cells, the cells are washed three times and resuspended in a physiological medium preferably sterile, at a convenient concentration (e.g., $1 \times 10^7$/ml) for injection in a patient. The cell suspension is then filtered, e.g., through sterile 110 mesh and put into Fenwall transfer packs. Samples of the cells are tested for the presence of microorganisms including fungi, aerobic and anaerobic bacteria, and mycoplasma In certain embodiments, inoculation of the cells is preferably through systemic administration. The cells can be administered intravenously through a central venous catheter or into a large peripheral vein. Other methods of administration (for example, direct infusion into an artery or direct infusion into the neural tissue, e.g. via a cannula) are within the scope of the invention. Approximately $1 \times 10^8$ cells are infused initially and the remainder are infused over the following several hours. In some regimens, patients may optionally receive in addition a suitable dosage of a neurogrophic or neurogenerative factor as described herein and/or a biological response modifier including but not limited to the cytokines IFN-α, IFN-γ, IL-2, IL-4, IL-6, TNF or other cytokine growth factor, antisense TGFβ, antisense IL-10, and the like. Thus, in some patients, recombinant human IL-2 may be used and will be infused intravenously every 8 hours beginning at the time of cell infusion. Injections of IL2 will preferably be at doses of 10,000 to 100,000 units/kg bodyweight, as previously used in cancer patients (Rosenberg et al. (1985) *N. Engl. J. Med.* 313: 1485). The IL-2 infusion may be continued for several days after infusion of the activated T cells if tolerated by the patient.

II. Assays for Agents that Modulate Neurotrophic and/or Neurogenerative Factor Expression and/or that Modulate Neural Protection or Neural Repair As indicated above, in one aspect, this invention is premised on the discovery that certain neurotrophic and/or neurogenerative factor can mitigate one or more symptoms associated with ischemia and/or induce repair/regeneration of neural cells and/or tissues and/or act in a neuroprotective capacity. Thus, agents that upregulate the expression and/or activity of these neurotrophic and/or neurogenerative factors are also expected prophylactic and/or therapeutic utility in subjects experiencing ischemia and/or at risk for ischemia.

Thus, in one embodiment, this invention provides methods of screening for agents that neurogenerative activity (e.g. by modulating expression or activity of neurotrophic and/or neurogenerative factors such as SCF, VEGF, FGF-2, and the like).

The methods typically involve detecting alterations in the expression level and/or activity level of a neurogenic and/or neurotrophic gene or gene product (e.g. SCF, VEGF, FGF-2) caused by the treatment with one or more of the agent(s) in question. An elevated expression level or activity level produced by the agent as, e.g., compared to a negative control where the test agent is absent or at reduced concentration indicates that the agent upregulates activity or expression of the factor(s) in question. Conversely, decreased expression level or activity level resulting from treatment by the agent as compared to a negative control where the test agent is absent or at reduced concentration indicates that the agent downregulates neurotrophic and/or neurogenerative factor activity or expression Expression levels of a gene can be altered by changes in by changes in the transcription of the gene product (i.e. transcription of mRNA), and/or by changes in translation of the gene product (i.e. translation of the protein), and/or by post-translational modification(s) (e.g. protein folding, glycosylation, etc.). Thus preferred assays of this invention typically contacting a test cell, tissue, or animal with one or more test agents, and assaying for level of transcribed mRNA (or other nucleic acids derived from the neurotrophic and/or neurogenerative factor gene(s)), level of translated protein, activity of translated protein, etc. Examples of such approaches are described below.

A) Nucleic-acid Based Assays

1) Target Molecules

Changes in expression level can be detected by measuring changes in mRNA and/or a nucleic acid derived from the mRNA (e.g. reverse-transcribed cDNA, etc.). In order to measure the neurotrophic and/or neurogenerative factor (e.g. SCF, EGF, HB-EGF, FGF-2, etc.) expression level it is desirable to provide a nucleic acid sample for such analysis. In preferred embodiments the nucleic acid is found in or derived from a biological sample. The term "biological sample", as used herein, refers to a sample obtained from an organism or from components (e.g., cells) of an organism. The sample may be of any biological tissue or fluid. Biological samples may also include organs or sections of tissues such as frozen sections taken for histological purposes.

The nucleic acid (e.g., mRNA nucleic acid derived from mRNA) is, in certain preferred embodiments, isolated from the sample according to any of a number of methods well known to those of skill in the art. Methods of isolating mRNA are well known to those of skill in the art. For example, methods of isolation and purification of nucleic acids are described in detail in by Tijssen ed., (1993) Chapter 3 of *Laboratory Techniques in Biochemistry and Molecular Biology: Hybridization With Nucleic Acid Probes, Part I. Theory and Nucleic Acid Preparation,* Elsevier, N.Y. and Tijssen ed.

In a preferred embodiment, the "total" nucleic acid is isolated from a given sample using, for example, an acid guanidinium-phenol-chloroform extraction method and polyA+ mRNA is isolated by oligo dT column chromatography or by using (dT)n magnetic beads (see, e.g., Sambrook et al., *Molecular Cloning: A Laboratory Manual* (2nd ed.), Vols. 1-3, Cold Spring Harbor Laboratory, (1989), or *Current Protocols in Molecular Biology,* F. Ausubel et al., ed. Greene Publishing and Wiley-Interscience, New York (1987)).

Frequently, it is desirable to amplify the nucleic acid sample prior to assaying for expression level. Methods of amplifying nucleic acids are well known to those of skill in the art and include, but are not limited to polymerase chain reaction (PCR, see. e.g., Innis, et al., (1990) *PCR Protocols. A guide to Methods Application.* Academic Press, Inc. San Diego,), ligase chain reaction (LCR) (see Wu and Wallace (1989) *Genomics* 4: 560, Landegren et al. (1988) *Science* 241: 1077, and Barringer et al. (1990) *Gene* 89: 117, transcription amplification (Kwoh et al. (1989) *Proc. Natl. Acad. Sci. USA* 86: 1173), self-sustained sequence replication (Guatelli et al. (1990) *Proc. Nat. Acad. Sci. USA* 87: 1874), dot PCR, and linker adapter PCR, etc.).

In a particularly preferred embodiment, where it is desired to quantify the transcription level (and thereby expression) of factor(s) of interest in a sample, the nucleic acid sample is one in which the concentration of the neurotrophic and/or neurogenerative factor mRNA transcript(s), or the concentration of the nucleic acids derived from the neurotrophic and/or neurogenerative factor mRNA transcript(s), is proportional to the transcription level (and therefore expression level) of that gene. Similarly, it is preferred that the hybridization signal intensity be proportional to the amount of hybridized nucleic acid. While it is preferred that the proportionality be relatively strict (e.g., a doubling in transcription rate results in a doubling in mRNA transcript in the sample nucleic acid pool and a doubling in hybridization signal), one of skill will appreciate that the proportionality can be more relaxed and even non-linear. Thus, for example, an assay where a 5 fold difference in concentration of the target mRNA results in a 3 to 6 fold difference in hybridization intensity is sufficient for most purposes.

Where more precise quantification is required, appropriate controls can be run to correct for variations introduced in sample preparation and hybridization as described herein. In addition, serial dilutions of "standard" target nucleic acids (e.g., mRNAs) can be used to prepare calibration curves according to methods well known to those of skill in the art. Of course, where simple detection of the presence or absence of a transcript or large differences of changes in nucleic acid concentration is desired, no elaborate control or calibration is required.

In the simplest embodiment, the nucleic acid sample is the total mRNA or a total cDNA isolated and/or otherwise derived from a biological sample (e.g. a sample from a neural cell or tissue). The nucleic acid may be isolated from the sample according to any of a number of methods well known to those of skill in the art as indicated above.

2) Hybridization-based Assays

Using the known sequence of neurotrophic and/or neurogenerative factor(s) of interest (e.g. SCF, VEGF, FGF-2, etc.) detecting and/or quantifying the transcript(s) can be routinely accomplished using nucleic acid hybridization techniques (see, e.g., Sambrook et al. supra). For example, one method for evaluating the presence, absence, or quantity of reverse-transcribed cDNA involves a "Southern Blot". In a Southern Blot, the DNA (e.g., reverse-transcribed neurotrophic and/or neurogenerative factor mRNA), typically fragmented and separated on an electrophoretic gel, is hybridized to a probe specific for the nucleic acid encoding the neurotrophic and/or neurogenerative factors of interest. Comparison of the intensity of the hybridization signal from the target specific probe with a "control" probe (e.g. a probe for a "housekeeping gene) provides an estimate of the relative expression level of the target nucleic acid.

Alternatively, the target factor mRNA can be directly quantified in a Northern blot. In brief, the mRNA is isolated from a given cell sample using, for example, an acid guanidinium-phenol-chloroform extraction method. The mRNA is then electrophoresed to separate the mRNA species and the mRNA is transferred from the gel to a nitrocellulose membrane. As with the Southern blots, labeled probes are used to identify and/or quantify the target mRNA. Appropriate controls (e.g. probes to housekeeping genes) provide a reference for evaluating relative expression level.

An alternative means for determining the neurotrophic and/or neurogenerative factor expression level is in situ hybridization. In situ hybridization assays are well known (e.g., Angerer (1987) *Meth. Enzymol* 152: 649). Generally, in situ hybridization comprises the following major steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application.

In some applications it is necessary to block the hybridization capacity of repetitive sequences. Thus, in some embodiments, tRNA, human genomic DNA, or Cot-1 DNA is used to block non-specific hybridization.

3) Amplification-based Assays

In another embodiment, amplification-based assays can be used to measure neurotrophic and/or neurogenerative factor expression (transcription) level. In such amplification-based assays, the target nucleic acid sequences (i.e., neurotrophic and/or neurogenerative factor nucleic acid) act as template(s) in amplification reaction(s) (e.g. Polymerase Chain Reaction (PCR) or reverse-transcription PCR (RT-PCR)). In a quantitative amplification, the amount of amplification product will be proportional to the amount of template in the original sample. Comparison to appropriate (e.g. healthy tissue or cells unexposed to the test agent) controls provides a measure of the neurotrophic and/or neurogenerative factor transcript level.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis et al. (1990) *PCR Protocols, A Guide to Methods and Applications,* Academic Press, Inc. N.Y.). One approach, for example, involves simultaneously co-amplifying a known quantity of a control sequence using the same primers as those used to amplify the target. This provides an internal standard that may be used to calibrate the PCR reaction.

One preferred internal standard is a synthetic AW106 cRNA. The AW106 cRNA is combined with RNA isolated from the sample according to standard techniques known to those of skill in the art. The RNA is then reverse transcribed using a reverse transcriptase to provide copy DNA. The cDNA sequences are then amplified (e.g., by PCR) using labeled primers. The amplification products are separated, typically by electrophoresis, and the amount of labeled nucleic acid (proportional to the amount of amplified product) is determined. The amount of mRNA in the sample is then calculated by comparison with the signal produced by the known AW106 RNA standard. Detailed protocols for quantitative PCR are provided in PCR Protocols, A Guide to Methods and Applications, Innis et al. (1990) Academic Press, Inc. N.Y. The known nucleic acid sequence(s) for neurotrophic and/or neurogenerative factor are sufficient to enable one of skill to routinely select primers to amplify any portion of the gene.

4) Hybridization Formats and Optimization of Hybridization a) Array-based Hybridization Formats In one embodiment, the methods of this invention can be utilized in array-based hybridization formats. Arrays are a multiplicity of different "probe" or "target" nucleic acids (or other compounds) attached to one or more surfaces (e.g., solid, membrane, or gel). In a preferred embodiment, the multiplicity of nucleic acids (or other moieties) is attached to a single contiguous surface or to a multiplicity of surfaces juxtaposed to each other.

In an array format a large number of different hybridization reactions can be run essentially "in parallel." This provides rapid, essentially simultaneous, evaluation of a number of hybridizations in a single "experiment". Methods of performing hybridization reactions in array based formats are well known to those of skill in the art (see, e.g., Pastinen (1997) *Genome Res.* 7: 606-614; Jackson (1996) *Nature Biotechnology* 14:1685; Chee (1995) *Science* 274: 610; WO 96/17958, Pinkel et al. (1998) *Nature Genetics* 20: 207-211).

Arrays, particularly nucleic acid arrays can be produced according to a wide variety of methods well known to those of skill in the art. For example, in a simple embodiment, "low density" arrays can simply be produced by spotting (e.g. by hand using a pipette) different nucleic acids at different locations on a solid support (e.g. a glass surface, a membrane, etc.).

This simple spotting, approach has been automated to produce high density spotted arrays (see, e.g., U.S. Pat. No. 5,807,522). This patent describes the use of an automated system that taps a microcapillary against a surface to deposit a small volume of a biological sample. The process is repeated to generate high density arrays.

Arrays can also be produced using oligonucleotide synthesis technology. Thus, for example, U.S. Pat. No. 5,143,854 and PCT Patent Publication Nos. WO 90/15070 and 92/10092 teach the use of light-directed combinatorial synthesis of high density oligonucleotide arrays. Synthesis of high density arrays is also described in U.S. Pat. Nos. 5,744,305, 5,800,992 and 5,445,934.

b) Other Hybridization Formats

As indicated above a variety of nucleic acid hybridization formats are known to those skilled in the art. For example, common formats include sandwich assays and competition or displacement assays. Such assay formats are generally described in Hames and Higgins (1985) *Nucleic Acid Hybridization, A Practical Approach,* IRL Press; Gall and Pardue (1969) *Proc. Natl. Acad. Sci. USA* 63: 378-383; and John et al. (1969) *Nature* 223: 582-587.

Sandwich assays are commercially useful hybridization assays for detecting or isolating nucleic acid sequences. Such assays utilize a "capture" nucleic acid covalently immobilized to a solid support and a labeled "signal" nucleic acid in solution. The sample will provide the target nucleic acid. The "capture" nucleic acid and "signal" nucleic acid probe hybridize with the target nucleic acid to form a "sandwich" hybridization complex. To be most effective, the signal nucleic acid should not hybridize with the capture nucleic acid.

Typically, labeled signal nucleic acids are used to detect hybridization. Complementary nucleic acids or signal nucleic acids may be labeled by any one of several methods typically used to detect the presence of hybridized polynucleotides.

The most common method of detection is the use of autoradiography with $^3H$, $^{125}I$, $^{35}S$, $^{14}C$, or $^{32}P$-labelled probes or the like. Other labels include ligands that bind to labeled antibodies, fluorophores, chemi-luminescent agents, enzymes, and antibodies which can serve as specific binding pair members for a labeled ligand.

Detection of a hybridization complex may require the binding of a signal generating complex to a duplex of target and probe polynucleotides or nucleic acids. Typically, such binding occurs through ligand and anti-ligand interactions as between a ligand-conjugated probe and an anti-ligand conjugated with a signal.

The sensitivity of the hybridization assays may be enhanced through use of a nucleic acid amplification system that multiplies the target nucleic acid being detected. Examples of such systems include the polymerase chain reaction (PCR) system and the ligase chain reaction (LCR) system. Other methods recently described in the art are the nucleic acid sequence based amplification (NASBAO, Cangene, Mississauga, Ontario) and Q Beta Replicase systems.

c) Optimization of Hybridization Conditions

Nucleic acid hybridization simply involves providing a denatured probe and target nucleic acid under conditions where the probe and its complementary target can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids, or in the addition of chemical agents, or the raising of the pH. Under low stringency conditions (e.g., low temperature and/or high salt and/or high target concentration) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

One of skill in the art will appreciate that hybridization conditions may be selected to provide any degree of stringency. In a preferred embodiment, hybridization is performed at low stringency to ensure hybridization and then subsequent washes are performed at higher stringency to eliminate mismatched hybrid duplexes. Successive washes may be performed at increasingly higher stringency (e.g., down to as low as 0.25×SSPE at 37° C. to 70° C.) until a desired level of hybridization specificity is obtained. Stringency can also be increased by addition of agents such as formamide. Hybridization specificity may be evaluated by comparison of hybridization to the test probes with hybridization to the various controls that can be present.

In general, there is a tradeoff between hybridization specificity (stringency) and signal intensity. Thus, in a preferred embodiment, the wash is performed at the highest stringency that produces consistent results and that provides a signal intensity greater than approximately 10% of the background intensity. Thus, in a preferred embodiment, the hybridized array may be washed at successively higher stringency solutions and read between each wash. Analysis of the data sets thus produced will reveal a wash stringency above which the hybridization pattern is not appreciably altered and which provides adequate signal for the particular probes of interest.

In a preferred embodiment, background signal is reduced by the use of a blocking reagent (e.g., tRNA, sperm DNA, cot-1 DNA, etc.) during the hybridization to reduce non-specific binding. The use of blocking agents in hybridization is well known to those of skill in the art (see, e.g., Chapter 8 in P. Tijssen, supra.)

Methods of optimizing hybridization conditions are well known to those of skill in the art (see, e.g., Tijssen (1993) *Laboratory Techniques in Biochemistry and Molecular Biology, Vol. 24: Hybridization With Nucleic Acid Probes,* Elsevier, N.Y.).

Optimal conditions are also a function of the sensitivity of label (e.g., fluorescence) detection for different combinations of substrate type, fluorochrome, excitation and emission bands, spot size and the like. Low fluorescence background surfaces can be used (see, e.g., Chu (1992) *Electrophoresis* 13:105-114). The sensitivity for detection of spots ("target elements") of various diameters on the candidate surfaces can be readily determined by, e.g., spotting a dilution series of fluorescently end labeled DNA fragments. These spots are then imaged using conventional fluorescence microscopy. The sensitivity, linearity, and dynamic range achievable from the various combinations of fluorochrome and solid surfaces (e.g., glass, fused silica, etc.) can thus be determined. Serial dilutions of pairs of fluorochrome in known relative proportions can also be analyzed. This determines the accuracy with which fluorescence ratio measurements reflect actual fluorochrome ratios over the dynamic range permitted by the detectors and fluorescence of the substrate upon which the probe has been fixed.

d) Labeling and Detection of Nucleic Acids

The probes used herein for detection of neurotrophic and/or neurogenerative factor expression levels can be full length or less than the full length of the neurotrophic and/or neurogenerative factor mRNA. Shorter probes are empirically tested for specificity. Preferred probes are sufficiently long so as to specifically hybridize with the neurotrophic and/or neurogenerative factor target nucleic acid(s) under stringent conditions. The preferred size range is from about 20 bases to the length of the neurotrophic and/or neurogenerative factor mRNA, more preferably from about 30 bases to the length of the neurotrophic and/or neurogenerative factor mRNA, and most preferably from about 40 bases to the length of the neurotrophic and/or neurogenerative factor mRNA.

The probes are typically labeled, with a detectable label. Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like, see, e.g., Molecular Probes, Eugene, Oreg., USA), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold (e.g., gold particles in the 40-80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

A fluorescent label is preferred because it provides a very strong signal with low background. It is also optically detectable at high resolution and sensitivity through a quick scanning procedure. The nucleic acid samples can all be labeled with a single label, e.g., a single fluorescent label. Alternatively, in another embodiment, different nucleic acid samples can be simultaneously hybridized where each nucleic acid sample has a different label. For instance, one target could have a green fluorescent label and a second target could have a red fluorescent label. The scanning step will distinguish sites of binding of the red label from those binding the green fluorescent label. Each nucleic acid sample (target nucleic acid) can be analyzed independently from one another.

Suitable chromogens which can be employed include those molecules and compounds which absorb light in a distinctive range of wavelengths so that a color can be observed or, alternatively, which emit light when irradiated with radiation of a particular wave length or wave length range, e.g., fluorescers.

Desirably, fluorescent labels should absorb light above about 300 nm, preferably about 350 nm, and more preferably above about 400 nm, usually emitting at wavelengths greater than about 10 nm higher than the wavelength of the light absorbed. It should be noted that the absorption and emission characteristics of the bound dye can differ from the unbound dye. Therefore, when referring to the various wavelength ranges and characteristics of the dyes, it is intended to indicate the dyes as employed and not the dye which is unconjugated and characterized in an arbitrary solvent.

Detectable signal can also be provided by chemiluminescent and bioluminescent sources. Chemiluminescent sources include a compound which becomes electronically excited by a chemical reaction and can then emit light which serves as the detectable signal or donates energy to a fluorescent acceptor. Alternatively, luciferins can be used in conjunction with luciferase or lucigenins to provide bioluminescence.

Spin labels are provided by reporter molecules with an unpaired electron spin which can be detected by electron spin resonance (ESR) spectroscopy. Exemplary spin labels include organic free radicals, transitional metal complexes, particularly vanadium, copper, iron, and manganese, and the like. Exemplary spin labels include nitroxide free radicals.

The label may be added to the target (sample) nucleic acid(s) prior to, or after the hybridization. So called "direct labels" are detectable labels that are directly attached to or incorporated into the target (sample) nucleic acid prior to hybridization. In contrast, so called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes providing a label that is easily detected. For a detailed review of methods of labeling nucleic acids and detecting labeled hybridized nucleic acids see *Laboratory Techniques in Biochemistry and Molecular Biology, Vol. 24: Hybridization With Nucleic Acid Probes,* P. Tijssen, ed. Elsevier, N.Y., (1993)).

Fluorescent labels are easily added during an in vitro transcription reaction. Thus, for example, fluorescein labeled UTP and CTP can be incorporated into the RNA produced in an in vitro transcription.

The labels can be attached directly or through a linker moiety. In general, the site of label or linker-label attachment is not limited to any specific position. For example, a label may be attached to a nucleoside, nucleotide, or analogue thereof at any position that does not interfere with detection or hybridization as desired. For example, certain Label-ON Reagents from Clontech (Palo Alto, Calif.) provide for labeling interspersed throughout the phosphate backbone of an oligonucleotide and for terminal labeling at the 3' and 5' ends. As shown for example herein, labels can be attached at positions on the ribose ring or the ribose can be modified and even eliminated as desired. The base moieties of useful labeling reagents can include those that are naturally occurring or modified in a manner that does not interfere with the purpose to which they are put. Modified bases include but are not limited to 7-deaza A and G, 7-deaza-8-aza A and G, and other heterocyclic moieties.

It will be recognized that fluorescent labels are not to be limited to single species organic molecules, but include inorganic molecules, multi-molecular mixtures of organic and/or inorganic molecules, crystals, heteropolymers, and the like. Thus, for example, CdSe-CdS core-shell nanocrystals enclosed in a silica shell can be easily derivatized for coupling to a biological molecule (Bruchez et al. (1998) *Science,* 281: 2013-2016). Similarly, highly fluorescent quantum dots (zinc sulfide-capped cadmium selenide) have been covalently coupled to biomolecules for use in ultrasensitive biological detection (Warren and Nie (1998) *Science,* 281: 2016-2018).

B) Polypeptide-based Assays

1) Assay Formats

In addition to, or in alternative to, the detection of neurotrophic and/or neurogenerative factor nucleic acid expression level(s), alterations in expression of neurotrophic and/or neurogenerative factor can be detected and/or quantified by detecting and/or quantifying the amount and/or activity of translated neurotrophic and/or neurogenerative factor polypeptide.

2) Detection of Expressed Protein

The neurotrophic and/or neurogenerative factor polypeptide(s) can be detected and quantified by any of a number of methods well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, western blotting, and the like.

In one preferred embodiment, the neurotrophic and/or neurogenerative factor polypeptide(s) are detected/quantified in an electrophoretic protein separation (e.g. a 1- or 2-dimensional electrophoresis). Means of detecting proteins using electrophoretic techniques are well known to those of skill in the art (see generally, R. Scopes (1982) Protein Purification, Springer-Verlag, N.Y.; Deutscher, (1990) *Methods in Enzymology Vol. 182: Guide to Protein Purification,* Academic Press, Inc., N.Y.).

In another preferred embodiment, Western blot (immunoblot) analysis is used to detect and quantify the presence of polypeptide(s) of this invention in the sample. This technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the target polypeptide(s).

The antibodies specifically bind to the target polypeptide(s) and may be directly labeled or alternatively may be subsequently detected using labeled antibodies (e.g., labeled sheep anti-mouse antibodies) that specifically bind to the a domain of the antibody.

In preferred embodiments, the neurotrophic and/or neurogenerative factor polypeptide(s) are detected using an immunoassay. As used herein, an immunoassay is an assay that utilizes an antibody to specifically bind to the analyte (e.g., the target polypeptide(s)). The immunoassay is thus characterized by detection of specific binding of a polypeptide of this invention to an antibody as opposed to the use of other physical or chemical properties to isolate, target, and quantify the analyte.

Any of a number of well recognized immunological binding assays (see, e.g., U.S. Pat. Nos. 4,366,241; 4,376,110; 4,517,288; and 4,837,168) are well suited to detection or quantification of the polypeptide(s) identified herein. For a review of the general immunoassays, see also Asai (1993) *Methods in Cell Biology Volume* 37: *Antibodies in Cell Biology,* Academic Press, Inc. New York; Stites & Terr (1991) *Basic and Clinical Immunology 7th Edition.*

Immunological binding assays (or immunoassays) typically utilize a "capture agent" to specifically bind to and often immobilize the analyte (neurotrophic and/or neurogenerative factor). In preferred embodiments, the capture agent is an antibody.

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled polypeptide or a labeled antibody that specifically recognizes the already bound target polypeptide. Alternatively, the labeling agent may be a third moiety, such as another antibody, that specifically binds to the capture agent/polypeptide complex.

Other proteins capable of specifically binding immunoglobulin constant regions, such as protein A or protein G may also be used as the label agent. These proteins are normal constituents of the cell walls of streptococcal bacteria. They exhibit a strong non-immunogenic reactivity with immunoglobulin constant regions from a variety of species (see, generally Kronval, et al. (1973) *J. Immunol.,* 111: 1401-1406, and Akerstrom (1985) *J. Immunol.,* 135: 2589-2542).

Preferred immunoassays for detecting the target polypeptide(s) are either competitive or noncompetitive. Noncompetitive immunoassays are assays in which the amount of captured analyte is directly measured. In one preferred "sandwich" assay, for example, the capture agents (antibodies) can be bound directly to a solid substrate where they are immobilized. These immobilized antibodies then capture the target polypeptide present in the test sample. The target polypeptide thus immobilized is then bound by a labeling agent, such as a second antibody bearing a label.

In competitive assays, the amount of analyte (neurotrophic and/or neurogenerative factor) present in the sample is measured indirectly by measuring the amount of an added (exogenous) analyte displaced (or competed away) from a capture agent (antibody) by the analyte present in the sample. In one competitive assay, a known amount of, in this case, labeled polypeptide is added to the sample and the sample is then contacted with a capture agent. The amount of labeled polypeptide bound to the antibody is inversely proportional to the concentration of target polypeptide present in the sample.

In one particularly preferred embodiment, the antibody is immobilized on a solid substrate. The amount of target polypeptide bound to the antibody may be determined either by measuring the amount of target polypeptide present in an polypeptide/antibody complex, or alternatively by measuring the amount of remaining uncomplexed polypeptide.

The immunoassay methods of the present invention include an enzyme immunoassay (EIA) which utilizes, depending on the particular protocol employed, unlabeled or labeled (e.g., enzyme-labeled) derivatives of polyclonal or monoclonal antibodies or antibody fragments or single-chain antibodies that bind neurotrophic and/or neurogenerative facto(s), either alone or in combination. In the case where the antibody that binds the neurotrophic and/or neurogenerative factor is not labeled, a different detectable marker, for example, an enzyme-labeled antibody capable of binding to the monoclonal antibody which binds the neurotrophic and/or neurogenerative factor, can be employed. Any of the known modifications of EIA, for example, enzyme-linked immunoabsorbent assay (ELISA), may also be employed. As indicated above, also contemplated by the present invention are immunoblotting immunoassay techniques such as western blotting employing an enzymatic detection system.

The immunoassay methods of the present invention can also include other known immunoassay methods, for example, fluorescent immunoassays using antibody conjugates or antigen conjugates of fluorescent substances such as fluorescein or rhodamine, latex agglutination with antibody-coated or antigen-coated latex particles, haemagglutination with antibody-coated or antigen-coated red blood corpuscles, and immunoassays employing an avidin-biotin or strepavidin-biotin detection systems, and the like.

The particular parameters employed in the immunoassays of the present invention can vary widely depending on various factors such as the concentration of antigen in the sample, the nature of the sample, the type of immunoassay employed and the like. Optimal conditions can be readily established by those of ordinary skill in the art. In certain embodiments, the amount of antibody that binds the neurotrophic and/or neurogenerative factor is typically selected to give 50% binding of detectable marker in the absence of sample. If purified antibody is used as the antibody source, the amount of antibody used per assay will generally range from about 1 ng to about 100 ng. Typical assay conditions include a temperature range of about 4° C. to about 45° C., preferably about 25° C. to about 37° C., and most preferably about 25° C., a pH value range of about 5 to 9, preferably about 7, and an ionic strength varying from that of distilled water to that of about 0.2M sodium chloride, preferably about that of 0.15M sodium chloride. Times will vary widely depending upon the nature of the assay, and generally range from about 0.1 minute to about 24 hours. A wide variety of buffers, for example PBS, may be employed, and other reagents such as salt to enhance ionic strength, proteins such as serum albumins, stabilizers, biocides and non-ionic detergents can also be included.

The assays of this invention are scored (as positive or negative or quantity of target polypeptide) according to standard methods well known to those of skill in the art. The particular method of scoring will depend on the assay format and choice of label. For example, a Western Blot assay can be scored by visualizing the colored product produced by the enzymatic label. A clearly visible colored band or spot at the correct molecular weight is scored as a positive result, while the absence of a clearly visible spot or band is scored as a negative. The intensity of the band or spot can provide a quantitative measure of target polypeptide concentration.

Antibodies for use in the various immunoassays described herein, are commercially available or can be produced using standard methods well know to those of skill in the art.

It will also be recognized that antibodies can be prepared by any of a number of commercial services (e.g., Berkeley antibody laboratories, Bethyl Laboratories, Anawa, Eurogenetec, etc.).

C) Assay Optimization

The assays of this invention have immediate utility in screening for agents that modulate the expression or activity of neurotrophic and/or neurogenerative factors (e.g. SCF, FGF-2, VEGF, etc.) by a cell, tissue or organism. The assays of this invention can be optimized for use in particular contexts, depending, for example, on the source and/or nature of the biological sample and/or the particular test agents, and/or the analytic facilities available. Thus, for example, optimization can involve determining optimal conditions for binding assays, optimum sample processing conditions (e.g. preferred PCR conditions), hybridization conditions that maximize signal to noise, protocols that improve throughput, etc. In addition, assay formats can be selected and/or optimized according to the availability of equipment and/or reagents. Thus, for example, where commercial antibodies or ELISA kits are available it may be desired to assay protein concentration. Conversely, where it is desired to screen for modulators that alter transcription the neurotrophic and/or neurogenerative factor gene, nucleic acid based assays are preferred.

Routine selection and optimization of assay formats is well known to those of ordinary skill in the art.

III. Pre-Screening for Agents that Bind a Neurotrophic and/or Neurogenerative Factor In certain embodiments it is desired to pre-screen test agents for the ability to interact with (e.g. specifically bind to) a neurotrophic and/or neurogenerative factor or to a nucleic acid encoding such a factor. Specifically binding test agents are more likely to interact with and thereby modulate neurotrophic and/or neurogenerative factor expression and/or activity. Thus, in some preferred embodiments, the test agent(s) are pre-screened for binding to neurotrophic and/or neurogenerative factor nucleic acids or to neurotrophic and/or neurogenerative factor proteins before performing the more complex assays described above.

In one embodiment, such pre-screening is accomplished with simple binding assays. Means of assaying for specific binding or the binding affinity of a particular ligand for a nucleic acid or for a protein are well known to those of skill in the art. In preferred binding assays, the neurotrophic and/or neurogenerative factor protein or nucleic acid is immobilized and exposed to a test agent (which can be labeled), or alternatively, the test agent(s) are immobilized and exposed to an neurotrophic and/or neurogenerative factor protein or to a neurotrophic and/or neurogenerative factor nucleic acid (which can be labeled). The immobilized moiety is then washed to remove any unbound material and the bound test agent or bound neurotrophic and/or neurogenerative factor nucleic acid or protein is detected (e.g. by detection of a label attached to the bound molecule). The amount of immobilized label is proportional to the degree of binding between the neurotrophic and/or neurogenerative factor protein or nucleic acid and the test agent.

IV. Scoring the Assays

As indicated above, methods of screening for modulators of neurotrophic and/or neurogenerative factor expression typically involve contacting a cell, tissue, organism, animal with one or more test agents and evaluating changes in neurotrophic and/or neurogenerative factor nucleic acid transcription and/or translation or neurotrophic and/or neurogenerative factor protein expression or activity. To screen for potential modulators, the assays described above are performed in the after administering and/or in the presence of one or more test agents using biological samples from cells and/or tissues and/or organs and/or organisms exposed to one or more test agents. The neurotrophic and/or neurogenerative factor activity and/or expression level is determined and, in a preferred embodiment, compared to the activity level(s) observed in "control" assays (e.g., the same assays lacking the test agent). A difference between the neurotrophic and/or neurogenerative factor expression and/or activity in the "test" assay as compared to the control assay indicates that the test agent is a "modulator" of neurotrophic and/or neurogenerative factor expression and/or activity.

In a preferred embodiment, the assays of this invention level are deemed to show a positive result, e.g. elevated expression and/or activity of neurotrophic and/or neurogenerative factor, when the measured protein or nucleic acid level or protein activity is greater than the level measured or known for a control sample (e.g. either a level known or measured for a normal healthy cell, tissue or organism mammal of the same species not exposed to the or putative modulator (test agent), or a "baseline/reference" level determined at a different tissue and/or a different time for the same individual). In a particularly preferred embodiment, the assay is deemed to show a positive result when the difference between sample and "control" is statistically significant (e.g. at the 85% or greater, preferably at the 90% or greater, more preferably at the 95% or greater and most preferably at the 98% or greater confidence level).

V. High Throughout Screening

The assays of this invention are also amenable to "high-throughput" modalities. Conventionally, new chemical entities with useful properties (e.g., modulation of neurotrophic and/or neurogenerative factor expression or activity) are generated by identifying a chemical compound (called a "lead compound") with some desirable property or activity, creating variants of the lead compound, and evaluating the property and activity of those variant compounds. However, the current trend is to shorten the time scale for all aspects of drug discovery. Because of the ability to test large numbers quickly and efficiently, high throughput screening (HTS) methods are replacing conventional lead compound identification methods.

In one preferred embodiment, high throughput screening methods involve providing a library containing a large number of compounds (candidate compounds) potentially having the desired activity. Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A) Combinatorial Chemical Libraries

Recently, attention has focused on the use of combinatorial chemical libraries to assist in the generation of new chemical compound leads. A combinatorial chemical library is a collection of diverse chemical compounds generated by either chemical synthesis or biological synthesis by combining a number of chemical "building blocks" such as reagents. For example, a linear combinatorial chemical library such as a polypeptide library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. For example, one commentator has observed that the systematic, combinatorial mixing of 100 interchangeable chemical building blocks results in the theoretical synthesis of 100 million tetrameric compounds or 10 billion pentameric compounds (Gallop et al. (1994) 37(9): 1233-1250).

Preparation and screening of combinatorial chemical libraries is well known to those of skill in the art. Such combinatorial chemical libraries include, but are not limited to, peptide libraries (see, e.g., U.S. Pat. No. 5,010,175, Furka (1991) *Int. J. Pept. Prot. Res.*, 37: 487493, Houghton et al.

(1991) *Nature,* 354: 84-88). Peptide synthesis is by no means the only approach envisioned and intended for use with the present invention. Other chemistries for generating chemical diversity libraries can also be used. Such chemistries include, but are not limited to: peptoids (PCr Publication No WO 91/19735, 26 Dec. 1991), encoded peptides (PCT Publication WO 93/20242, 14 Oct. 1993), random bio-oligomers (PCT Publication WO 92/00091, 9 Jan. 1992), benzodiazepines (U.S. Pat. No. 5,288,514), diversomers such as hydantoins, benzodiazepines and dipeptides (Hobbs et al., (1993) *Proc. Nat. Acad. Sci. USA* 90: 6909-6913), vinylogous polypeptides (Hagihara et al. (1992) *J. Amer. Chem. Soc.* 114: 6568), nonpeptidal peptidomimetics with a Beta-D-Glucose scaffolding (Hirschmann et al., (1992) *J. Amer. Chem. Soc.* 114: 9217-9218), analogous organic syntheses of small compound libraries (Chen et al. (1994) *J. Amer. Chem. Soc.* 116: 2661), oligocarbamates (Cho, et al., (1993) *Science* 261:1303), and/ or peptidyl phosphonates (Campbell et al., (1994) *J. Org. Chem.* 59: 658). See, generally, Gordon et al., (1994) *J. Med. Chem.* 37:1385, nucleic acid libraries (see, e.g., Strategene, Corp.), peptide nucleic acid libraries (see, e.g., U.S. Pat. No. 5,539,083) antibody libraries (see, e.g., Vaughn et al. (1996) *Nature Biotechnology,* 14(3): 309-314), and PCT/US96/ 10287), carbohydrate libraries (see, e.g., Liang et al. (1996) *Science,* 274: 1520-1522, and U.S. Pat. No. 5,593,853), and small organic molecule libraries (see, e.g., benzodiazepines, Baum (1993) C&EN, January 18, page 33, isoprenoids U.S. Pat. No. 5,569,588, thiazolidinones and metathiazanones U.S. Pat. No. 5,549,974, pyrrolidines U.S. Pat. Nos. 5,525, 735 and 5,519,134, morpholino compounds U.S. Pat. No. 5,506,337, benzodiazepines U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

A number of well known robotic systems have also been developed for solution phase chemistries. These systems include automated workstations like the automated synthesis apparatus developed by Takeda Chemical Industries, LID. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

B) High Throughput Assays of Chemical Libraries

Any of the assays for agents that modulate expression of neurotrophic and/or neurogenerative factor or that alter the binding specificity and/or activity of neurotrophic and/or neurogenerative factor polypeptides are amenable to high throughput screening. As described above, having determined particular neurotrophic and/or neurogenerative factor associated with repair of damaged neural tissue, likely modulators can have significant therapeutic value. Preferred assays thus detect increases of transcription (i.e., increases of nRNA production) by the test compound(s), increases of protein expression by the test compound(s), or binding to the gene (e.g., gDNA, or cDNA) or gene product (e.g., mRNA or expressed protein) by the test compound(s). Alternatively, the assay can detect inhibition of the characteristic activity of the neurotrophic and/or neurogenerative factor polypeptide.

High throughput assays for the presence, absence, or quantification of particular nucleic acids or protein products are well known to those of skill in the art. Similarly, binding assays are similarly well known. Thus, for example, U.S. Pat. No. 5,559,410 discloses high throughput screening methods for proteins, U.S. Pat. No. 5,585,639 discloses high throughput screening methods for nucleic acid binding (ie., in arrays), while U.S. Pat. Nos. 5,576,220 and 5,541,061 disclose high throughput methods of screening for ligand/antibody binding.

In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols the various high throughput. Thus, for example, Zymark Corp. provides technical bulletins describing screening systems for detecting the modulation of gene transcription, ligand binding, and the like.

V. Kits

In still another embodiment, this invention provides kits for practice of the assays or use of the compositions described herein. In one preferred embodiment, the kits comprise one or more containers containing antibodies and/or nucleic acid probes and/or substrates suitable for detection of neurotrophic and/or neurogenerative factor expression and/or activity levels. The kits can optionally include any reagents and/or apparatus to facilitate practice of the assays described herein. Such reagents include, but are not limited to buffers, labels, labeled antibodies, labeled nucleic acids, filter sets for visualization of fluorescent labels, blotting membranes, and the like.

In another embodiment, the kits can comprise a container containing a neurotrophic and/or neurogenerative factor, or a vector encoding a neurotrophic and/or neurogenerative factor and/or a cell comprising a vector encoding a neurotrophic and/or neurogenerative factor protein.

In addition, the kits can, optionally,include instructional materials containing directions (i.e., protocols) for the practice of the assay methods of this invention or the administration of the compositions described here along with counterindications. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Stem Cell Factor Stimulates Neurogenesis In Vitro and In Vivo

Cerebral ischemia stimulates neurogenesis in proliferative zones of the rodent forebrain. In this example, to identify the signaling factors involved, cerebral cortical cultures prepared from embryonic mouse brains were deprived of oxygen. Hypoxia increased bromodeoxyuridine (BrdU) incorporation into cells that expressed proliferation markers and immature neuronal markers and that lacked evidence of DNA damage or caspase-3 activation. Hypoxia-conditioned medium and stem cell factor (SCF), which was present in hypoxia-conditioned medium at increased levels, also stimulated BrdU incorporation into normoxic cultures. The SCF receptor, c-kit, was expressed in neuronal cultures and in neuroproliferative zones of the adult rat brain, and in vivo administration of SCF increased BrdU labeling of immature neurons in these regions. Cerebral hypoxia and ischemia may stimulate neurogenesis through trophic factors, including SCF.

The adult vertebrate brain retains the capacity for neurogenesis, which resides largely in selected regions that harbor neuronal precursor cells throughout life. These include the subventricular zone (SVZ), especially that portion adjacent to the most rostral parts of the lateral ventricles (Kirschenbaum and Goldman (19950 *Proc. Natl. Acad. Sci. USA*. 92: 210-214; Lois and Alvarez-Buylla (1993) *Proc. Natl. Acad. Sci. USA*. 90: 2074-2077; Luskin (1993) *Neuron*. 11: 173-189), and the subgranular zone (SGZ) of the hippocampal dentate gyrus (DG) (AltMan (1963) *Anat. Rec*. 145: 573-591). Some reports suggest that additional regions, such as the cerebral neocortex, may also generate new neurons in the adult, but this is disputed (Rakic (2002) *Nature Rev. Neurosci*. 3: 65-71).

Understanding the signals that trigger neuronal proliferation in the brain in vivo could assist the development of cell-replacement therapy for neurological disorders such as stroke. Efforts to identify these signals have been aided by the ability to grow neuronal precursor cells in vitro. Several factors can stimulate neurogenesis in such systems, including EGF (Reynolds and Weiss (1992) *Science*. 255: 1707-1710), FGF-2 (Ray et al. (1993) *Proc. Natl. Acad. Sci. USA*. 90: 3602-3606), and brain-derived neurotrophic factor (BDNF) (Kirschenbaum and Goldman (19950 *Proc. Natl. Acad. Sci. USA*. 92: 210-214). In addition, some studies have shown that cultured progenitor cells (Kilpatrick and Bartlett (1993) *Neuron*. 10: 255-265; Taupin et al. (2000) *Neuron*. 28: 385-397; Temple (1989) *Nature*. 340: 471-473) or tissue explants containing axons that project to neuroproliferative zones (Dehay et al. (2001) *J. Neurosci*. 21: 201-214) release factors into conditioned medium that can regulate neurogenesis. In some cases, administration or overexpression of neurotrophic factors can enhance neurogenesis in neuroproliferative zones of the adult brain in vivo (Benraiss et al. (2001) *J. Neurosci*. 21: 6718-6731; Pencea et al. (2001) *J. Neurosci*. 21: 6706-6717; Wagner et al. (1999) *J. Neurosci*. 19: 6006-6016; Zigova et al. (1998) *Mol. Cell Neurosci*. 11: 234-245).

In addition to its role in development, neurogenesis also occurs in response to cerebral injury, including excitotoxic damage (Gould and Tanapat (1997) *Neuroscience*. 80: 427-436; Yoshimura et al. (2001) *Proc. Natl. Acad. Sci. USA*. 98: 5874-5879), seizures (Parent et al. (1997) *J. Neurosci*. 17: 3727-3738), and oxidative stress-induced apoptosis (Magavi et al. (2000) *Nature*. 405: 951-955). We have focused on the ability of cerebral ischemia to stimulate neurogenesis because of its potential implications for stroke recovery and treatment. In a previous study (Jin et al. (2001) *Proc. Natl. Acad. Sci. USA*. 98: 4710-4715), we found that focal ischemia caused by occlusion of the middle cerebral artery (MCA) in the rat for 90 minutes increased the incorporation of BrdU in the SGZ and SVZ bilaterally. Cells labeled with bromodeoxyuridine (BrdU) coexpressed proliferating cell nuclear antigen (PCNA) and the immature neuronal marker doublecortin. Other reports indicate that global cerebral ischemia triggers neurogenesis in the SGZ (Liu et al. (1998) *J. Neurosci*. 18: 7768-7778; Takagi et al. (1999) *Brain Res*. 831: 283-287), that focal cerebral ischemia induces neurogenesis in peri-infarction cortex (Gu et al. (2000) *J. Cereb. Blood Flow Metab*. 20: 1166-1173; Jiang et al. (2001) *Stroke*. 32: 1201-1207), and that FGF-2 may be responsible for the proliferation and differentiation of neuronal progenitor cells in DG after focal ischemia (Yoshimura et al. (2001) *Proc. Natl. Acad. Sci. USA* 98: 5874-5879). However, the biological basis of hypoxia- or ischemia-induced neurogenesis remains poorly understood.

To address this issue, we used embryonic mouse cerebral cortical cultures enriched in cells of neuronal lineage and deprived of oxygen to simulate ischemia (Koretz et al. (1994) *Brain Res*. 643: 334-337). The embryonic age at which cultures are prepared (embryonic day 16-17 [E16-17]) corresponds to a period of active cortical neurogenesis (Bayer and Altman (1995) Pp. 1041-1078 In: *The rat nervous system*. G. Paxinos, editor. Academic Press. San Diego, Calif., USA). Our results indicate that hypoxia induces neurogenesis in mouse cortical cultures and that this effect is mediated by secreted factors such as stem cell factor (SCF), which stimulates neurogenesis in cortical cultures and in SVZ and SGZ in vivo.

Methods

Cell Culture and in Vitro Hypoxia

Cerebral cortical cultures were prepared from 16-day Charles River CD1 mouse embryos as described (Jin et al. (2000) *Proc. Natl. Acad. Sci. USA*. 97: 10242-10247), except that Neurobasal medium containing 2% $B_{27}$ supplement, 2 mM glutamate, and 1% penicillin and streptomycin (Life Technologies Inc., Rockville, Md., USA) was used (Brewer et al. (1993) *J. Neurosci. Res*. 35: 567-576). After 4 days, one-half of the medium was replaced with Neurobasal medium containing 2% $B_{27}$, and experiments were conducted at 6-7 days. Cultures were placed in modular incubator chambers (Billups-Rothenberg, Del Mar, Calif., USA) for 0-24 hours at 37° C. in humidified 95% air/5% $CO_2$ (control) or humidified 95% $N_2$/5% $CO_2$ (hypoxia), then returned to normoxic conditions for the remainder, if any, of the 24 hours (Koretz et al. (1994) *Brain Res*. 643: 334-337).

Focal Cerebral Ischemia

Focal ischemia was induced in 280- to 300-g adult male Sprague-Dawley rats by intraluminal occlusion of the MCA with a suture as previously described (Jin et al. (2001) *Proc. Natl. Acad. Sci. USA*. 98: 4710-4715; Pulsinelli et al. (1982) *Ann. Neurol*. 11: 491-498). The suture was left in place for 90 minutes and then withdrawn, and rats were sacrificed 1 week later.

BrdU Labeling

BrdU (50 µg/ml; Sigma-Aldrich, St. Louis, Mo., USA) was added to cultures 20 minutes prior to the onset of exposure to hypoxia for 0 to 24 hours, and cultures were processed for immunostaining as described (Sun et al. (2001) *Proc. Natl. Acad. Sci. USA*. 98: 15306-15311). For in vivo studies, BrdU was administered intraperitoneally, as reported previously (Jin et al. (2001) *Proc. Natl. Acad. Sci. USA*. 98: 4710-4715).

BrdU-immunopositive Cell Counts

BrdU-positive cells in culture were counted in five fields per well (center and at 3, 6, 9, and 12 o'clock). In brain sections, BrdU-positive cells were counted in five to seven 50-∝m coronal sections per animal, spaced 200 µm apart, by a researcher blinded to the experimental conditions, using a Nikon E300 epifluorescence microscope equipped with a Magnifire digital color camera (Chip-Coolers Inc., Warwick, R.I., USA). Cells containing densely brown-stained nuclei with clear morphology were considered BrdU positive. Results were expressed as BrdU-positive cells per field or section.

Assays of DNA Strand Breaks

DNA single- and doublestrand breaks were detected by DNA polymerase I-mediated biotin-dATP nick translation (PANT) labeling, Klenow labeling, or TUNEL, as described previously (31, 32).

Immunocytochemistry

Cell cultures (Sun et al. (2001) Proc. Natl. Acad. Sci. USA. 98: 15306 15311) and brain sections (Jin et al. (2001) Proc. Natl. Acad. Sci. USA 98: 4710-4715) were processed for immunocytochemistry as described previously. Primary Ab's were: mouse monoclonal anti-BrdU (2 µg/ml, Roche, Indianapolis, Ind., USA); sheep polyclonal anti-BrdU (25 µg/ml; BIODESIGN International, Saco, Me., USA); mouse monoclonal anti-neuronal nuclear antigen (1:200; anti-NeuN), mouse monoclonal anti-PCNA (1:100), mouse monoclonal anti-CD11b (1:50), mouse monoclonal anti-CD146 (1:50), goat polyclonal anti-vimentin (1:40), and rabbit polyclonal anti-SCF (1:100) (Chemicon International, Temecula, Calif., USA); mouse monoclonal anti-microtubule-associated protein-2 (1:100; anti-MAP-2), mouse monoclonal anti-glial fibrillary acidic protein (1:400; GFAP), and rabbit polyclonal antifibronectin (1:400) (Sigma-Aldrich); rabbit polyclonal anti-phospho-histone H3 (1:150; Upstate Biotechnology Inc., Lake Placid, N.Y., USA); rat monoclonal anti-embryonic nerve cell adhesion molecule (1:100; anti-E-NCAM) (BD Transduction Laboratories, San Diego, Calif., USA); mouse monoclonal anti-CDC47 (1:100; Lab Vision Corporation, Fremont, Calif., USA); affinity-purified goat polyclonal anti-Neuro D (1:100; Santa Cruz Biotechnology Inc., Santa Cruz, Calif., USA); mouse monoclonal anti-nestin (1:400) and, anti-c-kit (1:100) (BD PharMingen, San Diego, Calif., USA); and rabbit polyclonal Ab against cleaved (17-20 kDa) caspase-3 (1:250; New England Biolabs Inc., Beverly, Mass., USA). Secondary Ab's were: FITC-conjugated goat anti-mouse IgG, FITC-conjugated rabbit anti-rat IgG, and FITC-conjugated rabbit antirabbit IgG (1:200; Vector Laboratories, Burlingame, Calif., USA), and FITC-conjugated pig anti-goat IgG, rhodamine-conjugated rat-absorbed donkey anti-mouse IgG, rhodamine-conjugated rat-absorbed donkey anti-rabbit IgG, and rhodamine-conjugated rat-absorbed donkey anti-sheep IgG (1:200; Jackson ImmunoResearch Laboratories Inc., West Grove, Pa., USA). DAPI (4,6-diamidine-2-phenylindole dihydrochloride; Vector Laboratories) was used to counterstain nuclei, and fluorescence signals were detected as described (20). Controls included omitting or preabsorbing the primary or omitting the secondary Ab.

Retroviral Infection

Humanized Renilla reniformis green fluorescent protein (hrGFP) was cloned downstream of the viral promoter of the pFB retroviral vector (Stratagene, La Jolla, Calif., USA). The vector was produced by transiently transfecting NIH 3T3 cells with two additional vectors expressing gag-pol and vesicular stomatitis virus G envelope protein. The pFB-hrGFP supernatant containing $4.9 \times 10^7$ or greater infectious virus particles was filtered through a 0.45-µm filter and frozen at −80° C. Ten microliters of retroviral supernatant was added to each well of four-well plates containing neuron cultures in 500 µl of medium, incubated at 37° C. for 2 days, and then for 24 hours in normoxic or hypoxic conditions. GFP-expressing cells were detected with a Nikon E300 microscope with excitation at 470 and emission at 505 nm.

Hypoxia-conditioned Medium

Medium (500 µl/well) was collected from normoxic or hypoxic cultures on four-well plates, pipetted into the sample reservoir of a Microcon YM-100 centrifugal filter device (Millipore Corp., Bedford, Mass., USA) that had been spin rinsed with medium and centrifuged according to the manufacturer's instructions. Constituents with relative molecular mass ($M_r$) greater than 100,000 were recovered by rinsing with 500 µl of medium, and constituents with $M_r$ less than 100,000 were transferred to a YM-50 filter device and the same steps repeated. Successive fractions were collected by applying the filtrates to YM30, YM10, and YM3 filter devices. Fractions (500 µl/well of a four-well plate) were added immediately to normoxic cultures together with BrdU, and in some cases pFB-hrGFP, for 24-72 hours.

Cell Viability

Cell viability was assayed by incubating cells with 3-(4,5-dimethylthiazol-2-yl)-2,5-diphenyl tetra-zolium bromide (MTT) (5 mg/ml; Sigma-Aldrich) at 37° C. for 2 hours. Medium was removed, and cells were solubilized with DMSO and transferred to 96-well plates. Absorbance at 570 nm was measured in a Cytofluor 4000 plate reader (PerSeptive Biosystems, Framingham, Mass., USA). Results were expressed as a percentage of control absorbance measured in normoxic cultures after subtracting background absorbance measured in freeze-thawed cultures.

Western Blotting

Blotting was performed as described previously (Jin et al. (2000) Proc. Natl. Acad. Sci. USA. 97: 10242-10247); in some experiments, protein from 1.5-2.0 ml of culture supernatant was concentrated using a Microcon YM-3 centrifugal filter device (Millipore Corp.). The primary Ab's were: rabbit polyclonal anti-SCF, mouse monoclonal anti-EGF, rabbit polyclonal anti-TNFα and rabbit polyclonal anti-FGF-2 (1:500; Chemicon International) and rat monoclonal anti-β-NGF (1:500, BD PharMingen). The secondary Ab's were: horseradish peroxidase-conjugated anti-mouse or anti-rat (for monoclonal primary) or anti-rabbit (for polyclonal primary) IgG (1:3,000; Santa Cruz Biotechnology Inc.). Differences in SCF protein expression on Western blots were quantified using a GS-710 calibrated imaging densitometer and Quantity One software (Bio-Rad Laboratories Inc., Hercules, Calif., USA).

RT-PCR

Total RNA was isolated from cultured neurons using TRIzol reagent (Life Technologies Inc.) according to the manufacturer's instructions. RT-PCR was performed using the following primers: FGF-2 forward primer, 5'-AGA GCG ACC CAC ACG TCA AAC-3' (160-181, SEQ ID NO:1) and FGF-2 reverse primer, 5'-CCA ACT GGA GTA TTT CCG TGA CC-3' (366-344, SEQ ID NO:2) designed from mouse FGF-2 (GenBank accession number M30644) and SCF forward primer, 5'-CGG GAA TCC TGT GAC TGA TAA TG-3' (236-258, SEQ ID NO:3) and SCF reverse primer, 5'-TGT CAG ATG CCA CCA TAA AGT CC-3' (605-627, SEQ ID NO:4) designed from mouse SCF (GenBank accession number M57647). Rat β-actin sense and antisense primers were used as controls for determining the quantity of RNA. PCR products were separated on 3% agarose gels using 100-bp ladder DNA standards as a size reference.

Intraventricular Administration of SCF

Adult male Sprague-Dawley rats were anesthetized with 4% isoflurane in 70% $N_2O$/30% $O_2$ and implanted with an osmotic minipump (Alzet 1003D; Alza Corporation, Mountain View, Calif., USA). The cannula was placed in the right lateral ventricle 4.0 mm deep to the pial surface, +0.8 mm anteroposterior relative to bregma, and 1.3 mm lateral to the midline. Each rat was infused for 3 days with 1 μl/h of either human recombinant SCF (1 μg/ml; R&D Systems Inc., Minneapolis, Minn., USA) in artificial cerebrospinal fluid (aCSF; 128 mM NaCl, 2.5 mM KCl, 0.95 mM $CaCl_2$, 1.99 mM $MgCl_2$) (n=6); SCF (1 μg/ml) plus anti-c-kit Ab (10 μg/ml) in aCSF (n=4) or aCSF alone (n=5). BrdU (50 mg/kg; Sigma-Aldrich) was dissolved in saline and given intraperitoneally, twice daily at 8-hour intervals, for 3 consecutive days, and rats were killed 1 week later. BrdU-positive cells were characterized by double-labeling with anti-NeuN and Neuro D Ab's as described (Jin et al. (2001) Proc. Natl. Acad. Sci. USA 98: 4710-4715). Confocal images were obtained with a Nikon PCN 2000 confocal microscope system.

Data Analysis

Quantitative data were expressed as mean plus or minus SEM from at least three experiments. ANOVA and Student t test were used for statistical analysis, with P values less than 0.05 considered significant.

Results

Hypoxia Induces Neurogenesis in Neuronal Cultures from Mouse Cerebral Cortex

In previous studies of in vitro hypoxia we used cortical cultures maintained for 10-19 days, which contained greater than 90% mature neurons. To determine the cellular composition of 6- to 7-day cultures, immunocytochemistry was performed using cell type-specific markers. As shown in FIG. 1, panels a and b, most cells expressed markers associated with immature neurons—Hu, E-NCAM, and βIII tubulin. Smaller percentages of cells expressed the neuroepithelial cell marker nestin, the mature neuronal marker calbindin, or the immature neuronal marker Neuro D. Some cells expressed both mature and immature neuronal markers, suggesting an intermediate stage of differentiation.

To determine if hypoxia stimulates BrdU incorporation, BrdU was added, and 20 minutes later cultures were placed in 95% $N_2$/5% $CO_2$ for up to 24 hours. Under these conditions, the number of BrdU-labeled cells increased by 4 hours and was maximal (~5 times control) at 8 hours (FIG. 1, panel c). To evaluate the possibility that BrdU labeling was due to DNA repair rather than replication, BrdU-labeled hypoxic cultures were assessed for DNA damage using the Klenow fragment of DNA polymerase I, PANT labeling, and TUNEL (Chen et al. (1997) J. Neurochem. 69: 232-245; Jin et al. (1999) J. Neurochem. 72: 1204-1214). DNA damage was detectable in only approximately 20% of BrdU-labeled cells after 8 hours of hypoxia (FIG. 2, panels a-c), and little overlap was seen between BrdU labeling and immunoreactivity for the 17- to 20-kDa cleavage product of activated caspase-3 (2, panel d), which is associated with hypoxic neuronal death in these cultures (Jin et al. (2001) Neuroscience. 108: 351-358). To investigate further whether BrdU labeled primarily dividing cells in our cultures, hypoxia was induced in the presence of the cell cycle inhibitors aphidicolin, cytosine arabinoside, and hydroxyurea. Each cell cycle inhibitor reduced BrdU incorporation into hypoxic cultures by up to approximately 60-80% (FIG. 1, panel d), consistent with the majority of BrdU labeling being associated with cell division.

BrdU labeling also colocalized with several markers of cell proliferation, including PCNA (FIG. 2, panel e), a cell cycle-dependent nuclear protein that acts in concert with DNA polymerase™ and helps to regulate the fidelity of DNA replication (Ino and Chiba (2000) Brain Res. Mol. Brain Res. 78: 163-174); phospho-histone-H3 (FIG. 2, panel f), a marker of mitotic chromosome condensation (Hendzel et al. (1997) Chromosoma. 106: 348-360); a green fluorescent protein-expressing retroviral vector (pFB-hrGFP) that infects dividing cells (FIG. 2, panel g); and the "replication-licensing" protein CDC47 FIG. 2, panel h) (Fujita et al. (1996) J. Bio. Chem. 271: 4349-4354).

Figure 2:
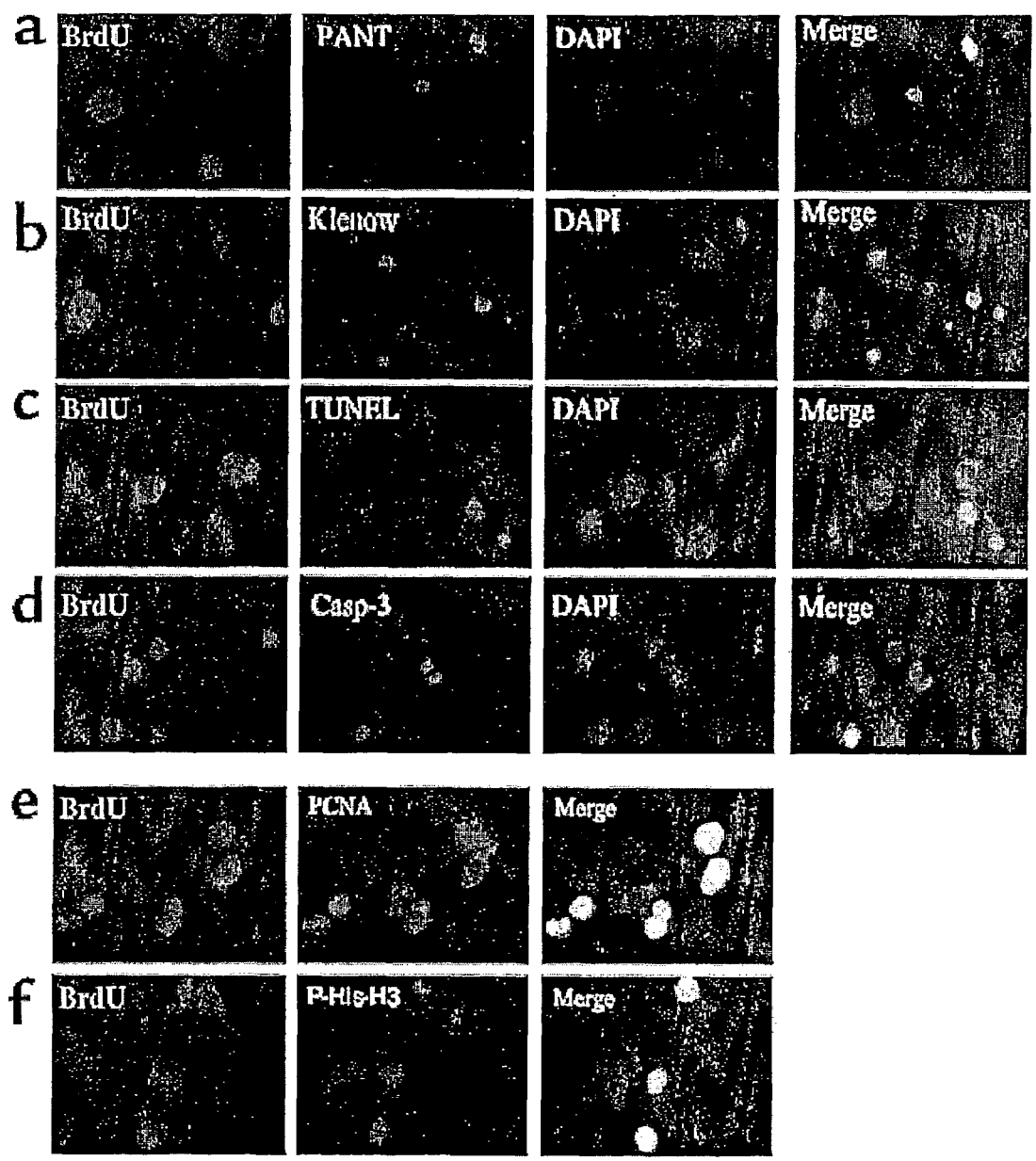
FIG. 2 shows that Hypoxia induces BrdU incorporation into uninjured cells that coexpress markers of proliferating cells and of immature, but not mature, neurons. Cerebral cortical cultures were treated with BrdU, exposed to hypoxia for 8 hours, and labeled with an Ab against BrdU and another marker, and nuclei were counterstained with DAPI. Most cells incorporating BrdU showed no evidence of DNA damage as assayed by PANT labeling (a), Klenow labeling (b), or TUNEL (c), or of caspase activation measured with an Ab against the 17- to 20-kDa caspase-3 cleavage product (d). BrdU incorporation colocalized with the cell proliferation markers PCNA (e) and phospho-histone-H3 (f), with retroviral infectivity reported by a GFP-expressing vector (g), and with the "replication-licensing" protein CDC47 (h). As shown in g, not all pFB-hrGFP-infected cells incorporated BrdU, which may be related to differences in labeling efficiency between the two markers. BrdU incorporation also colocalized with nestin (i) and to a large extent with E-NCAM (j), but not with the mature neuronal markers NeuN (k) and MAP-2 (l). Data are representative fields from at least three experiments per row.
Figure 2:
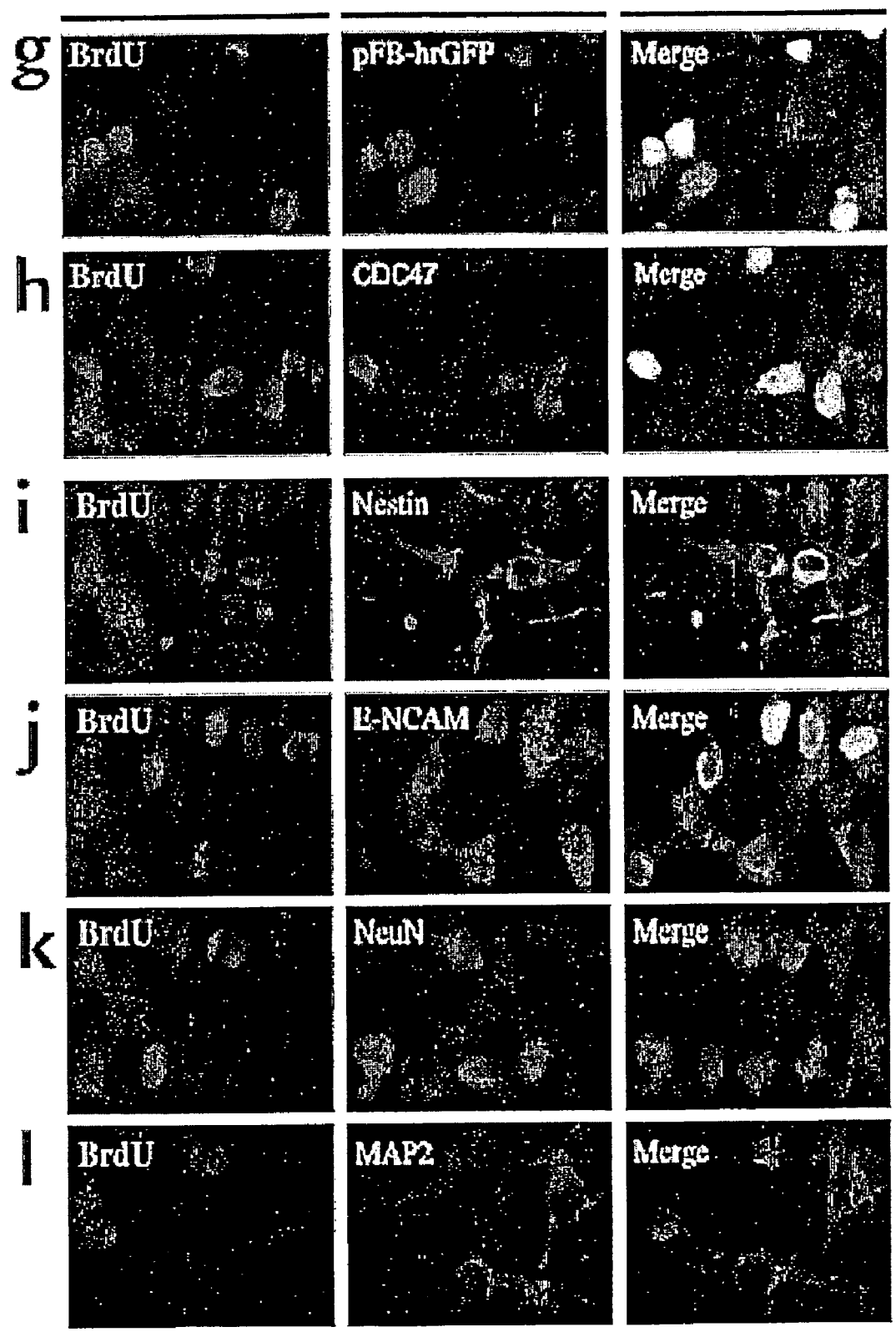

To determine the identity of the BrdU-labeled cells, cultures were examined for coexpression of two markers expressed by neuroepithelial precursor cells or immature neurons, nestin (Cattaneo and McKay (1990) Nature. 347: 762-765) and E-NCAM (Seki and Arai (1991) Neurosci. Res. 12: 503-513), and two markers expressed by mature neurons, NeuN and MAP-2. Most BrdU-labeled cells coexpressed nestin and E-NCAM, but not NeuN or MAP-2 (FIG. 2, panels i-l). This is additional evidence that BrdU incorporation is not simply due to DNA damage and repair, because DNA damage affects mature as well as immature neurons (Scharff (2000) Curr. Opin. Neurobiol. 10: 774-783). BrdU labeling was also absent from the rare (~1%) GPAP-immunopositive cells in these cultures.

Figure 3:
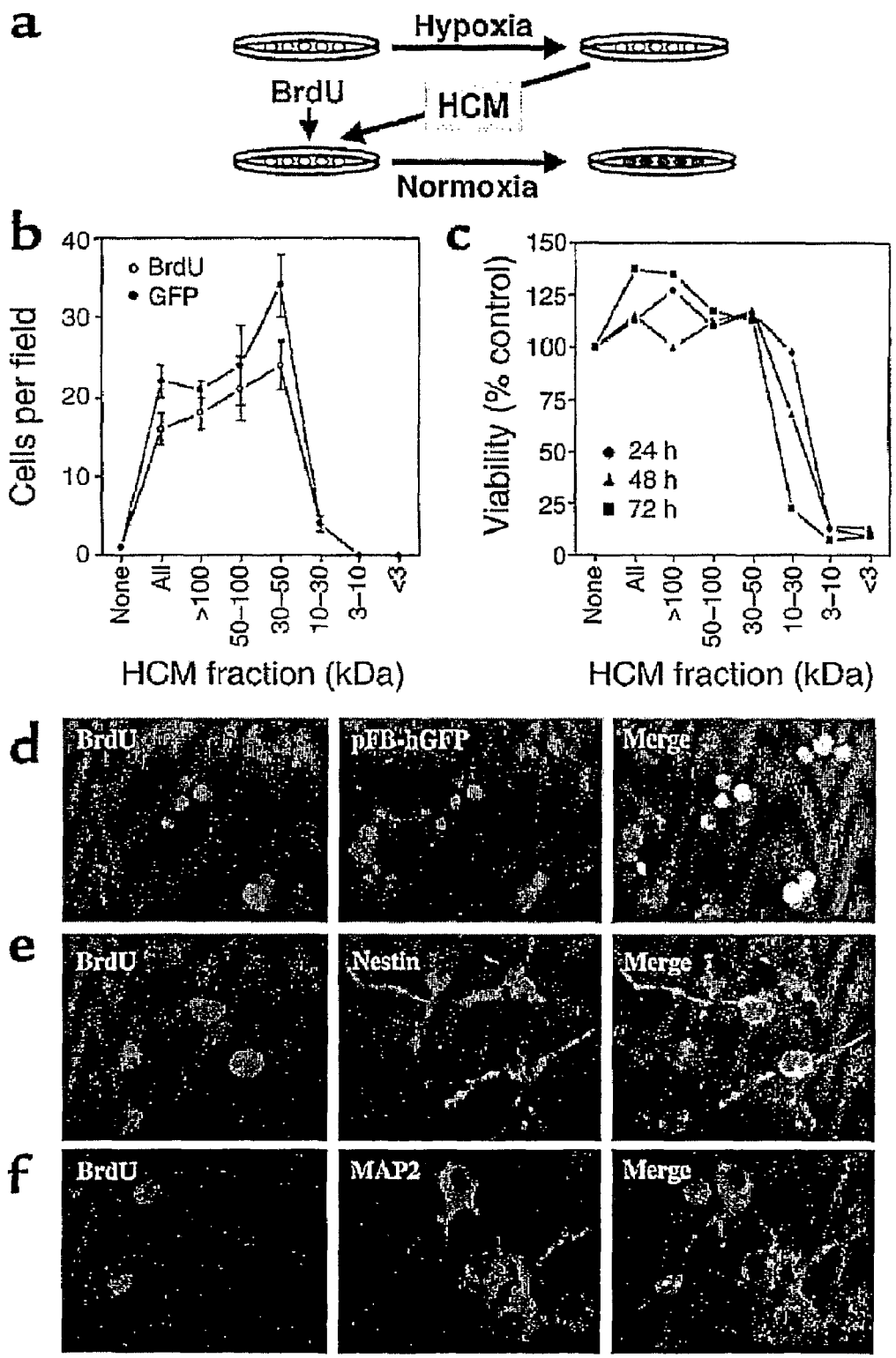
FIG. 3 shows that HCM transfers hypoxic stimulation of neurogenesis to normoxic cultures. Cerebral cortical cultures were exposed to normoxia or hypoxia for 8 hours, medium was removed, and normoxia-conditioned control medium (none), whole HCM (all), or HCM fractions were added to normoxic cultures, together with BrdU and, in some cases, pFB-hrGFP, for 24-72 hours (Panel a). Incubation for 72 hours with HCM fractions of more than 30 kDa increased the number of cells showing BrdU incorporation and GFP fluorescence (Panel b). HCM fractions of less than 30 kDa had no effect on BrdU or pFB-hrGFP labeling, but reduced cell viability at 24-72 hours as measured by MTT absorbance (Panel c). To characterize BrdU-labeled cells, cultures were exposed to hypoxia for 8 hours, medium was removed, and HCM was added to normoxic cultures, together with BrdU, and in some cases, pPB-hrGFP (panel d) for 72 hours. Some cultures were also stained with Ab's against nestin (Panel e) or MAP-2 (Panel f). BrdU incorporation colocalized with pFB-hrGFP infectivity and with nestin, but not MAP-2 immunostaining. Data are mean±SEM, n=3 (Panel b), mean values that varied by less than 10%, n=3 (Panel c), or representative fields from three experiments (Panels d-f).

Hypoxia-induced Neurogenesis is Mediated by a Soluble Factor that can Transfer Neuroproliferative Activity to Normoxic Cultures Focal cerebral ischemia induces BrdU incorporation in neuroproliferative zones remote from the site of injury (20), suggesting that brain lesions may release diffusible factors that can stimulate neurogenesis. If such factors also mediate hypoxia-induced neurogenesis in our cultures, it should be possible to transfer neuroproliferative activity via hypoxia-conditioned medium (HCM). To test this possibility, cultures were exposed to hypoxia for up to 24 hours, and HCM was removed and transferred to normoxic cultures. BrdU was added, and cultures were maintained under normoxic conditions for up to 72 hours (FIG. 3, panel a). As predicted, HCM stimulated an increase in BrdU incorporation into normoxic cultures (FIG. 3, panel b). Like hypoxia-induced BrdU labeling, HCM-induced labeling colocalized with markers of cell proliferation and of immature but not mature neurons (FIG. 3, panels d-f). Therefore, HCM can transfer the effect of hypoxia to normoxic cells.

Hypoxia-induced Proliferative Activity is Associated with Selected HCM Fractions To identify factors in HCM responsible for stimulating BrdU incorporation in our cultures, HCM was fractionated according to molecular weight by centrifugal filtration, and fractions were tested for their effects on cell viability and cell proliferation in normoxic cultures. Higher-molecular-weight (especially 30-50 kDa) fractions stimulated BrdU incorporation and increased the number of dividing (pFB-hrGFP infectible) cells in normoxic cultures (FIG. 3, panel b). However, when HCM and HCM fractions were boiled and then added to cultures, there was no difference in BrdU incorporation across treatments (P=0.148, ANOVA).

Neither whole HCM nor 30-kDa or greater fractions reduced the number of viable cells in cultures measured by MTT absorbance, but the 10- to 30-kDa fraction killed most cells by 72 hours and the 3- to 10-kDa and less than 3-kDa fractions killed almost all cells by 24 hours (FIG. 3, panel c).

The toxic factors in these fractions do not appear to include excitatory amino acids because L-glutamate did not reduce cell viability and glutamate antagonists failed to inhibit the toxicity of 30-kDa or lower HCM fractions (not shown).

Candidate Mediators of Hypoxia-induced Neurogenesis Include SCF and FGF-2

Figure 4:
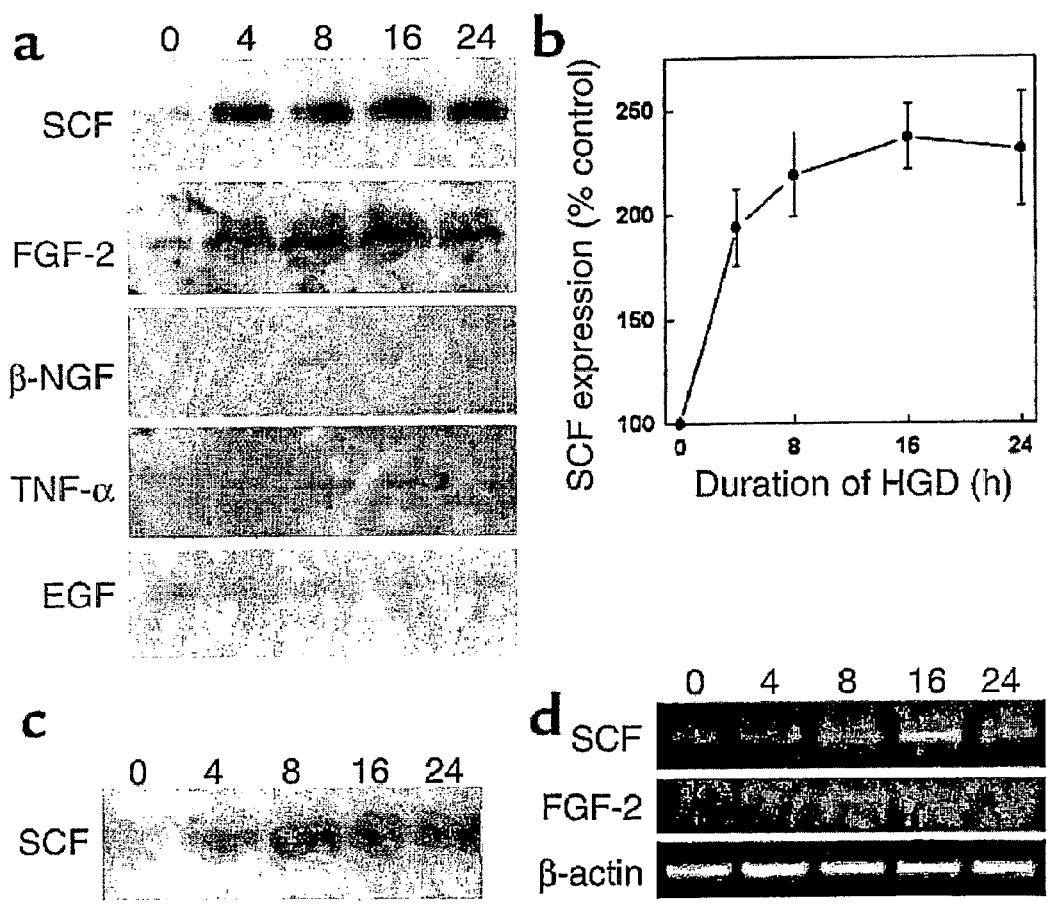
FIG. 4 shows that hypoxia induces expression of SCF and FGF-2 in vitro. Cerebral cortical cultures were exposed to hypoxia for up to 24 hours, and cellular expression of growth factors and cytokines was measured by Western blotting (Panel a), which showed increased expression of SCF and FGF-2 at 4-24 hours. SCF expression was quantified by computer densitometry (Panel b). SCF levels were also increased after the indicated periods of hypoxia (h) in culture supernatants (Panel c). Enhanced expression of SCF and FGF-2 was due to transcriptional activation, because RT-PCR showed increases in SCF and FGF-2 mRNA levels (Panel d). Data are representative blots from three experiments (Panels a, c, d) or mean±SEM, n=3 (Panel b).

Because maximal proliferative activity was associated with the 30- to 50-kDa fraction of HCM, because many growth factors fall within this range, and because several of these have been implicated in neurogenesis, we screened a series of growth factors for increased expression in hypoxic neuronal cultures. These included EGF, FGF-2, BDNF, nerve growth factor, IGF-I, TNF-<, TGF-<, glial cell line-derived neurotrophic factor, and SCF. SCF and FGF-2 protein and mRNA levels were increased in hypoxic cultures (FIG. 4, panels a, b, and d). Elevated levels of SCF in HCM were also demonstrable by Western blotting of concentrated supernatants from centrifuged cultures (FIG. 4, panel c). We focused our attention on SCF (also known as Steel factor, kit ligand, or mast cell growth factor), a secreted glycoprotein that migrates with an apparent molecular weight of 30-35 kDa (Molineux and McNiece (1998) Pp. 713-725 In *The cytokine handbook.* A. W. Thomson, editor. Academic Press. San Diego, Calif., USA). Mice with mutations in SCF or its receptor, c-kit, show amastocytosis, amelanocytosis, and sterility, providing evidence for the involvement of SCF in hematopoiesis, melanogenesis, and gametogenesis (Galli (1993) *N. Engl. J. Med.* 328: 257-265). SCF is also expressed in peripheral (Torihashi et al. (1996) *Brain Res.* 738: 323-328; Young et al. (1998) *Gastroenterology.* 115: 898-908) and central (Manova (1992) *J. Neurosci.* 12: 4663-4676; Wong and Licinio (1994) *Neuroimmunomodulation.* 1: 181-187; Zhang and Fedoroff (1997) *J. Neurosci. Res.* 47: 1-15) neurons, has neurotrophic effects (Carnahan et al. (1994) *J. Neurosci.* 14: 1433-1440; Hirata et al. (1993) *Development.* 119: 49-56; Langtimm-Sedlak et al. (1996) *Dev. Biol.* 174: 345-359), regulates neurosecretory function (Kovacs et al. (1996) *J. Neuroimmunol.* 65: 133-141). Moreover, SCF mutations are associated with abnormal development of sensory neurons (Lourenssen et al. (2000) *Neuroreport.* 11: 1159-1165) and defects in hippocampus dependent learning (Motro et al. (1996) *Proc. Natl. Acad. Sci. USA.* 93: 1808-1813). Finally, traumatic brain injury can increase neuronal SCF expression (Zhang and Fedoroff (1999 (*Acta Neuropathol.* (*Berl.*) 97: 393-398). However, SCF has not been implicated in neurogenesis.

Figure 5:
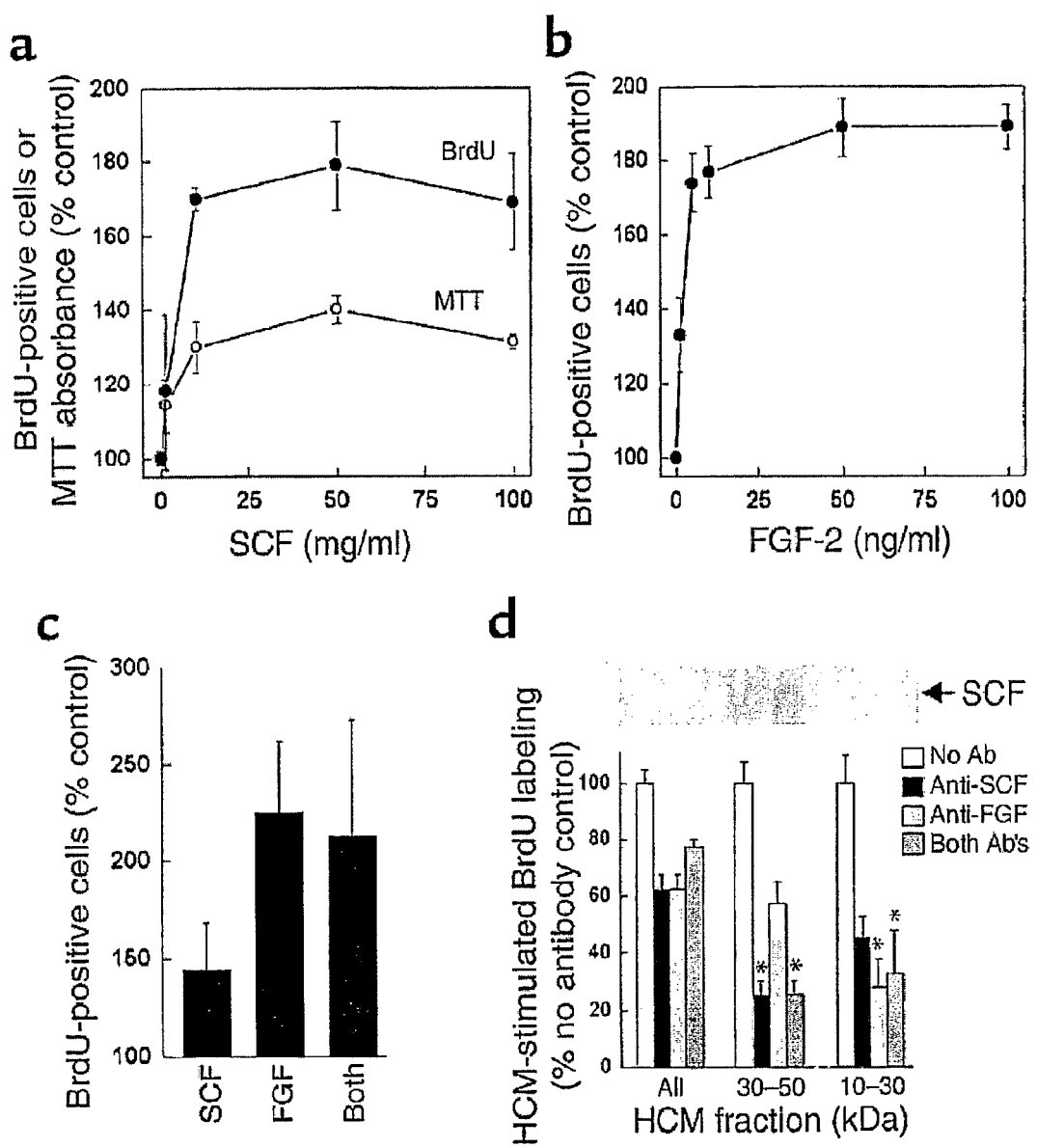
FIG. 5 shows that SCF and FGF-2 stimulate BrdU incorporation in vitro. Treatment of normoxic cultures for 24 hours with SCF increased both the number of cells incorporating BrdU and the number of viable cells measured by MTT absorbance (Panel a). FGF-2 also increased BrdU incorporation in these cultures (Panel b), but the effects of maximally effective concentrations (10 ng/ml) of SCF and FGF-2 were not additive (Panel c). Ab's against SCF and FGF-2 each reduced the component of BrdU labeling stimulated by unfractionated HCM (all) by approximately 40%, but these effects were not additive Panel d). Anti-SCF and the combination of anti-SCF plus anti-FGF-2 (but not anti-FGF-2 alone) reduced BrdU labeling stimulated by the 30- to 50-kDa fraction of HCM by approximately 75%, consistent with the preferential localization of immunoreactive SCF to this fraction on Western blots. Anti-FGF-2 and the combination of anti-FGF-2 plus anti-SCF (but not anti-SCF alone) reduced BrdU labeling stimulated by the 10- to 30-kDa fraction of HCM by approximately 70%, consistent with the Mr value of 17.2 kDa for FGF-2. Data are mean±SEM, n=3, or representative blots from three experiments (inset to panel d). Asterisks in panel d indicate that the percentage of inhibition of BrdU labeling by a given Ab or combination of Ab's is significantly different in that HCM fraction than in unfractionated HCM ($P<0.05$; ANOVA and post hoc Student-Newman-Keuls tests).

If SCF contributes to the neuroproliferative effect of HCM, then a similar effect should be achieved by treating normoxic cultures with SCF alone. When SCF was added to cultures for 24 hours at concentrations comparable to those found in circulating blood and those associated with half-maximal effects of SCF in in vitro colony-forming assays (2-9 ng/ml) (Molineux and McNiece (1998) Pp. 713-725 In *The cytokine handbook.* A. W. Thomson, editor. Academic Press. San Diego, Calif., USA), we observed an increase of approximately 75% in the number of cells labeled with BrdU (FIG. 5, panel a). We also observed an increase of approximately 40% in MTT absorbance, consistent with an increase in the number of viable cells in culture. FGF-2 also stimulated BrdU incorporation (FIG. 5, panel b), but the effects of maximally effective concentrations (10 ng/ml) of SCF and FGF-2 were not additive (FIG. 5, panel c). When HCM was treated with Ab's against SCF or FGF-2, stimulation of BrdU labeling was reduced by approximately 40%, but the effects of the two Ab's were not additive (FIG. 5, panel d). Anti-SCF preferentially reduced BrdU labeling stimulated by the 30- to 50-kDa fraction of HCM, consistent with the $M_r$ value for SCF (30-35 kDa), whereas anti-FGF-2 was more effective in inhibiting the effect of the 10- to 30-kDa fraction of HCM, consistent with the $M_r$ value for FGF-2 (17.2 kDa).

Figure 6:
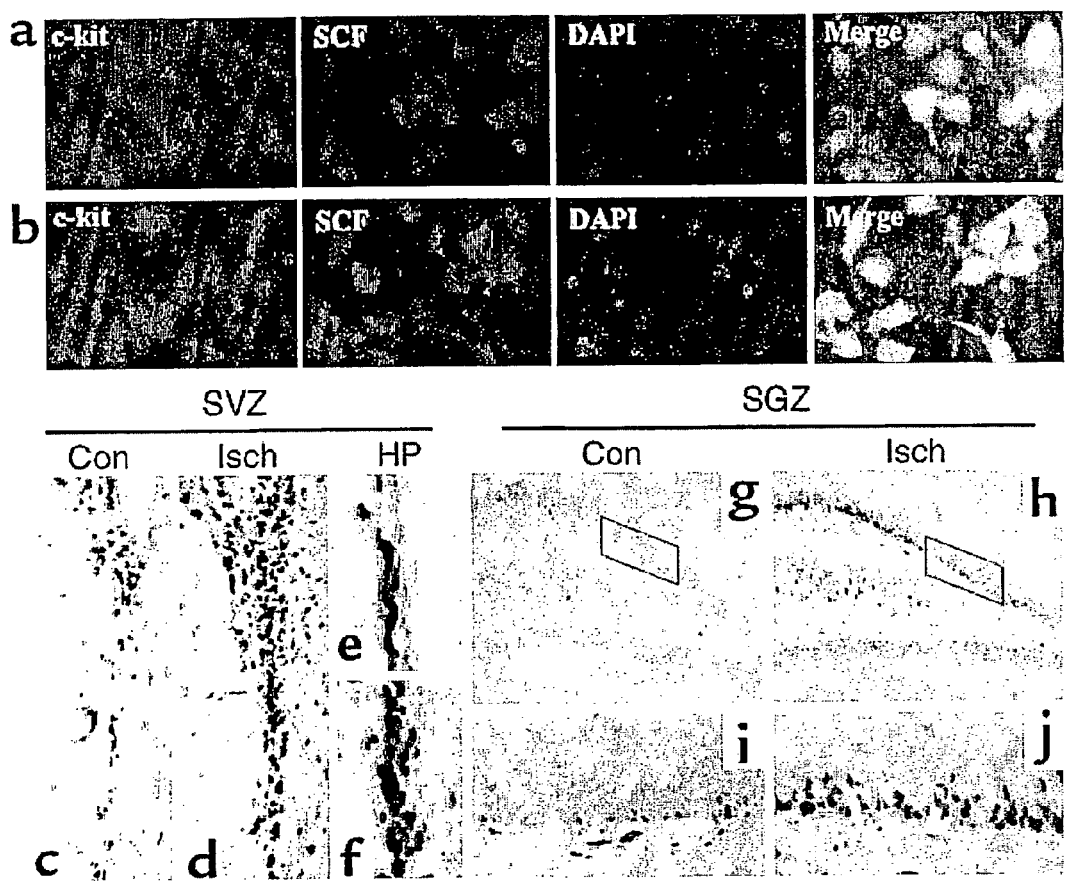
FIG. 6 illustrates c-kit expression in vitro and in SVZ and SGZ of normal and ischemic rat brain in vivo. Normoxic cerebral cortical cultures (Panel a) and cultures deprived of oxygen for 8 hours (Panel b) were stained with Ab's against c-kit and SCF and with DAPI. Brain sections through SVZ (Panels c-f) and SGZ of DG (Panels g-j) were also immunostained with an Ab against c-kit, which was visualized with DAB. c-kit was expressed in SVZ (Panels c and e) and SGZ (Panels g and i) of normal brain (Con), and expression was increased 24 hours after MCA occlusion (Isch) in the ipsilateral SVZ (Panels d and f) and SGZ (Panels h and j). (Panels c, d, g, and h)×200. (Panels e, f, i, and j)×400 (HP). Data are representative fields from at least three experiments per panel.

The effects of SCF, including its effects on neurons, are mediated through the c-kit receptor tyrosine kinase (Linnekin (1999) *Int. J. Biochem. Cell Biol.* 31: 1053-1074), and embryonic cortical neurons express c-kit in culture (Zhang and Fedoroff (1997) *J. Neurosci. Res.* 47: 1-15). To confirm that c-kit was expressed in our cultures, immunocytochemistry was performed with Ab's against SCF and against c-kit. In normoxic cultures, most cells expressed c-kit, while a more restricted population of cells expressed high levels of SCF (FIG. 6, panel a). After 8 hours of hypoxia, however, most cells expressed both c-kit and SCF (FIG. 6, panel b).

SCF Stimulates Neurogenesis In Vivo

To evaluate if SCF acts as a neuroproliferative factor in the brain in vivo, we first examined if c-kit is expressed in neuroproliferative zones. As shown in FIG. 6, panels c-j, c-kit was expressed in both SVZ and SGZ. Moreover, the number of c-kit-expressing cells increased in the ipsilateral hemisphere after cerebral ischemia induced by MCA occlusion. The presence of c-kit in SVZ and SGZ and its upregulation after ischemia are compatible with the involvement of SCF in stimulation of neurogenesis after cerebral ischemia.

Figure 7:
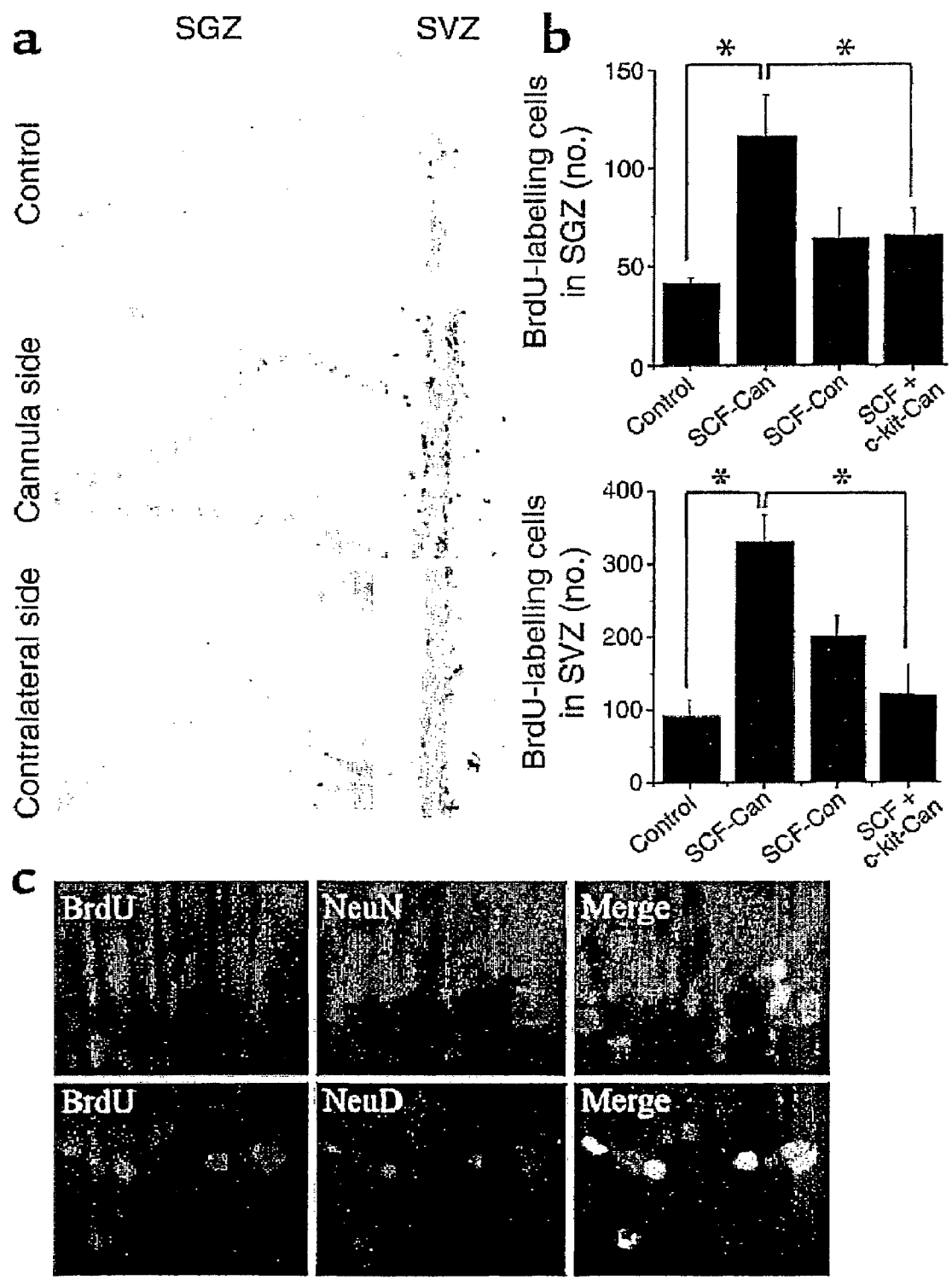
FIG. 7 shows that intraventricular SCF stimulates BrdU incorporation in SGZ and SVZ in vivo. (Panel a) Brain sections through SGZ and SVZ were immunostained with anti-BrdU Ab 1 week after intraventricular infusion of SCF or aCSF vehicle (n=6). Compared with aCSF (control), SCF increased the number of BrdU-positive cells in SGZ and SVZ. Proliferation was more pronounced on the cannula side, as compared with the contralateral side. (Panel b) BrdU-labeled cells in SGZ (top) and SVZ (bottom) were counted in control brain (n=6) and both ipsilateral (cannula side) and contralateral to SCF infusion (n=6). In some experiments, SCF was infused together with anti-c-kit Ab (n=4). Bars (left to right) represent control; SCF-treated, cannula side; SCF-treated, control side; and SCF- and anti-c-kit-treated, cannula side. BrdU-positive cells were increased in SVZ on both the infused and contralateral sides and in SGZ on the infused side. The effect of SCF was partially blocked by coadministration of anti-c-kit Ab (*$P<0.05$, Student t test). (Panel c) Rat brain sections through SGZ, obtained 1 week after SCF infusion, were double-labeled for BrdU (red) and NeuN or Neuro D (green). Merged images show that BrdU labeling colocalized with Neuro D and, in some cases, NeuN. Data shown are representative fields from the number of experiments given above (Panels a and c), or mean±SEM (n=3) (Panel b).

To test whether SCF can stimulate neurogenesis in vivo, adult rats were treated with SCF (infused into the right lateral ventricle) and BrdU (injected intraperitoneally) for 3 days, and sacrificed 1 week later. As shown in FIG. 7, panels a and b, the number of BrdU-immunopositive cells in SVZ and SGZ increased after SCF administration, especially ipsilateral to the infusion. The increase in BrdU labeling was abolished by coadministration of an anti-c-kit Ab, suggesting that the effect of SCF was mediated through c-kit.

To identify cells targeted to proliferate by SCF, sections from SGZ of SCF- and BrdU-treated rat brains 1 week after treatment were immunostained for BrdU and for markers of mature (NeuN) and immature (Neuro D) neurons (FIG. 7, panel c). These double-label studies showed that most BrdU-immunopositive cells coexpressed Neuro D and a few cells expressed NeuN. Therefore, SCF appears to stimulate proliferation of cells of neuronal lineage in vivo, most of which exhibit an immature neuronal phenotype at 1 week.

Discussion

Cerebral ischemia stimulates neurogenesis both locally (Liu et al. (1998) *J. Neurosci.* 18: 7768-7778; Takagi et al. (1999) *Brain Res.* 831: 283-287; Gu et al. (2000) *J. Cereb. Blood Flow Metab.* 20: 1166-1173; Jiang et al. (2001) *Stroke.* 32: 1201-1207) and at a distance (Yoshimura et al. (2001) *Proc. Natl. Acad. Sci. USA.* 98: 5874-5879; Jin et al. (2001) *Proc. Natl. Acad. Sci. USA.* 98: 4710-4715; Zhang et al. (2001) *Neuroscience.* 105: 33-41) and may even have the capacity to direct the fate of hematopoietic stem cells toward a neuronal phenotype (Chen et al. (2001) *Stroke.* 32: 1005-1011). One way such lesion-derived signaling might occur is through the release of trophic factors from injured tissue.

To begin to identify factors that might contribute to ischemia-induced neurogenesis, we modeled cerebral ischemia in neuronal cultures from embryonic mouse cerebral cortex. Hypoxia stimulated the incorporation of BrdU into cells that coexpressed phenotypic markers of proliferating cells and immature neurons, suggesting that they are dividing cells that might have the capacity to develop into mature, functional neurons. Next we transferred proliferative activity to normoxic cultures with HCM. Its effect was similar to that of hypoxia and was associated preferentially with HCM constituents of 30 kDa or greater. Among several possible mediators tested, SCF and FGF-2 were both upregulated in hypoxia-treated cultures, and both increased BrdU incorporation. Although synergistic effects of SCF and FGF-2 have been described in myeloid progenitor cells (Gabrilove et al. (1994) *Blood.* 83: 907-910), the effects of SCF and FGF-2 were not additive in our cultures, which could imply that they act through a shared signal transduction pathway. Alternatively, one of these growth factors could act through effects on the other: for example, SCF increases FGF-2 expression in mast cells (Qu et al. (1998) *Int. Arch. Allergy Immunol.* 115: 47-54) and FGF-2 increases SCF expression in several murine cell lines (Sugimoto et al. (1999) *J. Cell Physiol.* 181: 285-294).

SCF produces biological effects by activating c-kit, leading to receptor homodimerization and autophosphorylation and stimulating signal transduction pathways involving phosphatidylinositol-3-kinase, Src, JAK/STAT, and Ras-Raf-MAP kinase (54). In hematopoietic cells, SCF and c-kit regulate a variety of developmental events, including cell proliferation, survival, and differentiation (Ashman (1999) *Int. J. Biochem. Cell Biol.* 31: 1037-1051). An effect of SCF alone is insufficient to explain the neuroproliferative effects of hypoxia and HCM in our cultures, because the maximal percentage increase in BrdU incorporation observed with SCF was less than that seen with hypoxia or HCM and because neuroproliferative effects were associated with several HCM fractions and with FGF-2.

Several pitfalls can beset studies of this sort (Scharff (2000) *Curr. Opin. Neurobiol.* 10: 774-783). First, BrdU can label cells undergoing DNA repair, but we did not find evidence of DNA damage by PANT labeling, Klenow labeling, or TUNEL in most BrdU labeled cells. In addition, BrdU labeling colocalized with other markers of cell proliferation, including PCNA, phospho-histone-H3, and CDC47 (Fujita et al. (1996) *J. Biol. Chem.* 271: 4349-4354). Finally, BrdU immunoreactivity correlated with retroviral infectivity. Another issue is whether proliferating cells that express neuronal markers are necessarily destined to become neurons or simply exhibit ectopic expression of such markers as part of an injury response. The BrdU-labeled cells we studied in vitro expressed both nestin and E-NCAM, which suggests that they were neuroepithelial precursors or immature neurons. Whether they eventually would have expressed mature neuronal markers like NeuN and MAP-2, or electrophysiological neuronal properties if exposed to the proper combination and sequence of instructive signals in vivo, or achieve functional integration into an ischemic brain remains to be determined.

To address whether SCF stimulates neurogenesis in vivo, we examined whether (a) c-kit is expressed in neuroproliferative zones of the brain, (b) c-kit expression in SVZ and SGZ is altered after ischemia, (c) administration of SCF increases BrdU incorporation in SVZ and SGZ, and (d) cells in which SCF stimulates BrdU incorporation are of neuronal lineage. In all four cases, our results were affirmative, supporting a role for SCF in ischemia-induced neurogenesis in vivo.

The ability of an ischemic brain lesion to stimulate the proliferation of neuronal precursors invites speculation as to the possible role of such proliferation in functional recovery from stroke and the possibility that augmentation of neurogenesis, perhaps by the administration of one or more trophic factors, might have therapeutic potential. These issues are important because, although some degree of spontaneous recovery after stroke is the norm, the molecular and cellular mechanisms underlying recovery are poorly understood and existing treatment for stroke is generally applicable to only a small percentage of cases, or is limited in efficacy. Endogenous mechanisms of neuroprotection from ischemia, including mechanisms of neurogenesis, may hold clues for the development of improved therapy.

Example 2

1. Adult Neurogenesis In Vivo a) Increasing BrdU Incorporation into DG and SVZ after Ischemia Because neurogenesis persists in the adult mammalian brain and can be regulated by physiological and pathological events, we investigated its possible involvement in the brain's response to focal cerebral ischemia. Ischemia was induced by occlusion of the middle cerebral artery in the rat for 90 min, and proliferating cells were labeled with BrdU over 2-day periods prior to sacrificing animals 1, 2 or 3 week after ischemia. The brain regions examined for BrdU incorporation included Û SGZ and SVZ Û. We confirmed that neurogenesis occurs in these regions in normal rat brains. When brains of postischemic animals were stained for BrdU, there was increased labeling in the SGZ and SVZ. In the SGZ, more cells were labeled ipsilateral than contralateral to ischemia at 1 week. The labeled cells were irregularly distributed immediately subjacent to the DG granule cell layer. In the SVZ, the number of BrdU-labeled nuclei was about equal on the two sides of the brain. As expected, neither SGZ nor SVZ showed histological features of neuronal injury when stained with cresyl violet, nor evidence of DNA damage when assayed with the Klenow-labeling assay. In contrast, ischemic neuronal injury and DNA damage were prominent in areas like cerebral cortex and Cpu, which are supplied by the MCA and undergo infarction.

Brain regions were examined for BrdU incorporation. Sections through SVZ and DG from normal brain were stained for BrdU and visualized with DAB. BrdU-positive cells were detectable in both DG and SVZ in the normal brains.

Sections through DG and SVZ were stained for BrdU. BrdU labeling in SGZ was increased on the ipsilateral ischemic side relative to nonischemic control brains and the contralateral side at 1 week. But, the number of BrdU labeling cells in SVZ was about equal at 1 week.

b) Quantitation of Ischemia-Induced Increase in BrdU Incorporation

To quantify changes in BrdU labeling after ischemia, we counted BrdU-reactive nuclei in brain sections from sham-operated rats, and rats killed 1, 2, or 3 weeks after ischemia. The increase in BrdU labeling in the SVZ was similar in magnitude to that in the ipsilateral SGZ and to that produced by olfactory bulbectomy or growth factors. However, the pattern of postischemic BrdU labeling in the SVZ was different from that in the SGZ in that it was bilaterally symmetrical. In addition, labeling in the SVZ was maximal at 2 weeks rather than 1 week.

BrdU-reactive cells were counted in nonischemic brains and in ischemic brains on the ischemic side (ipsilateral) and nonischemic side (contralateral) at 1-3 weeks. Data are means±SEM. In DG, cell counts were increased at 1 week on both sides. In SVZ, cell counts were increased at both 1 and 2 weeks on both sides.

c) Relationship Between BrdU Labeling and NeuN Immunoreactivity

To characterize the cells labeled by BrdU after ischemia, we first performed double-labeling with antibodies against BrdU and NeuN, a neuron-specific nuclear protein. In DG, NeuN is first expressed after SGZ neuronal precursors migrate into the granule cell layer. BrdU and NeuN were seen in distinct non-overlapping cell populations, indicating that BrdU was not incorporated into mature neurons. Instead, BrdU labeling in DG was localized to the SGZ immediately underlying the NeuN-positive granule cell layer, where neuronal precursors reside and where global ischemia in gerbils stimulates neurogenesis. BrdU labeling in the SVZ was also discretely localized to a narrow band of NeuN-negative cells adjacent to the ventricle.

Double immunolabeling for BrdU (left, red) and NeuN (center, green) was performed in DG and SVZ from control brains (Con) and the ischemic sides of brains 1 week after MCAO (Isch). Merged images showed lack of coexpression of BrdU and NeuN and localize BrdU labeling to the SGZ of DG and the SVZ.

Double labeling for BrdU was performed in sections through DG ipsilateral to MCA occlusion, taken 1 week after ischemia. Merged images showed no coexpression of BrdU with Hu, but extensive coexpression of BrdU with DCX and PCNA.

d) Relationship Between BrdU Labeling and Hu, DCX, and PCNA Immunoreactivity

The absence of BrdU labeling in NeuN expressing cells and the confinement of BrdU labeling to known zones of neurogenesis after ischemia is consistent with labeling of neuronal precursors. To test this hypothesis, we double-labeled brain sections with antibodies against BrdU and three developmentally regulated marker proteins: Hu, a nuclear and cytoplasmic protein expressed early in neuronal maturation about the time precursors exit the cell cycle; DCX, a microtubule-associated protein found in the soma and processes of migrating neurons; and PCNA, which is involved in DNA replication and repair and is expressed in proliferating cells. In the ipsilateral SGZ 1 week after ischemia, there was little or no BrdU labeling of cells expressing Hu, but almost completely overlapping of BrdU labeling with DCX and PCNA expression. In the SVZ, there was also little or no overlap between BrdU labeling and Hu expression and essentially complete overlap between BrdU labeling and DCX expression. However, in contrast to SGZ, only a few cells that were labeled with BrdU expressed PCNA.

2. Neurogenesis from Marrow Stromal Cells (MSC) In Vitro a) MSC Characterization and Differentiation after Incubation with Neuronal Culture Medium MSC were isolated from the femurs of adult mice and propagated in vitro. MSC comprise three types based on morphology, including large, flat cells; spindle-shaped cells; and very small, round cells (termed rapidly self-renewing cells, or RS cells). MSC have been shown to differentiate into neuron-like cells when incubated with "differentiation medium" containing all-trans-retinoic acid (RA), BDNF and FGF, suggesting that soluble factors are important in MSC differentiation. Therefore, we explored whether supernatant from cortical neurons cultured in serum-free conditions contains such soluble factors, and whether they are able to induce MSC differentiation into neuron-like cells in vitro. MSC cultured under these conditions express NeuN and DCX after incubated with neuronal medium for 3 days, suggesting that cortical neuron culture supernatant contains factors that can induce MSC differentiation into neuronal cells. Mature and immature neuronal cell markers were detected in the same cells, suggesting that these cells are in the process of differentiation.

Normal MSC include morphologically distinct cell types: large flat cells, spindle-shaped cells, and small round cells. MSC cultured with the supernatant of cortical neurons for 3 days, followed by staining with NeuN (green) and DCX (red) and analysis by laser scanning confocal microscopy, showing that some MSC differentiated into neuron-like cells in vitro.

b) Induction of MSC Differentiation by SCF

We have evidence that the growth factor SCF increased BrdU incorporation into cortical neurons in vitro, indicating that SCF can function as a regulator of proliferation in cortical neurogenesis. Whether SCF promotes neuronal differentiation as well was investigated. When MSC were incubated with SCF (10 ng/ml for 3 days), some MSC differentiated in neuron-like cells with long processes. By analysis of immunocytochemistry, E-NCAM protein was greatly increased in the BMC after treatment with SCF, and GABA and glutamate were present. Although the glutamate seen may not be in the neurotransmitter pool, the presence of GABA is for a neuronal phenotype.

3. Neurogenesis from Bone Marrow-derived Cells In Vivo

Although transplantation of nervous system-derived precursors into local regions of brain produces differentiated neurons in vivo and improves deficits in models of some neurodegenerative diseases such as Parkinson's disease, there are several disadvantages of using these cells. Therefore, BMC may become a source of stem cells for treatment of CNS diseases and brain injury in the future. To explore this potential, BMC were isolated from transgenic mice that overexpress GFP (C57BL/6-GFP) and injected IP into normal, wild-type mice (C57BL/6) at $2.5 \times 10^7$ cells per mouse. Mice were sacrificed and the brain was removed 1 week later. BMC migration into the normal brain was detected by fluorescence microscopy. BMC were barely observable at this time. However, when BMC were transplanted IP in mice 30 min after the induction of focal cerebral ischemia (90 min), a marrow-derived cells, GFP-positive cells were observed in different brain regions, including DG, SVZ, caudate-putamne, OB and cerebral cortex.

BMC ($2.5 \times 10^7$/per animal) from mice with overexpression of GFP protein were administrated IP after induction of focal ischemia. Ischemic brains were removed and sectioned 1 week later. Migrant BMC with GFP-positive cytoplasm were detected by fluorescence microscopy. BMC (GFP+) were barely observed in sham-operated brain. Migrant BMC were detectable in DG on the ipsilateral and contralateral sides after ischemia, and some migrant cells were located in the SGZ. Migrant BMC were also detectable in cortex (Ctx), caudate-putamen (CPu), OB and SVZ after cerebral ischemia.

The distribution of migrant cells on the ipsilateral and contralateral sides was similar, which is consistent with the finding that neurogenesis from endogenous precursors was increased on both sides after focal ischemia. Immunocytochemistry showed that marrow-derived migrant cells expressed immature neuronal cell markers including E-NCAM, suggesting that migrant BMC differentiated into neuron-like cells after cerebral ischemia.

After BMC were given IP, ischemic brains were immunostained with the neuronal progenitor marker E-NCAM (red), followed by counterstaining with DAPI. Laser scanning confocal microscope analysis showed that marrow-derived cells, co-expressed the immature neuronal cell marker E-NCAM.

Example 3

Cerebral Neurogenesis Induced by Intranasal Administration of Growth Factors Neurogenesis, which is critical in brain development and continues into adulthood, can be stimulated by injury and may have a role in brain repair and associated functional recovery. Therefore, the ability to augment injury-induced neurogenesis could have therapeutic consequences for acute and chronic neurodegenerative disease. Growth factors, usually given by the intracerebroventricular route, are among the best characterized stimuli to neurogenesis in rodents, but their clinical usefulness is restricted by their limited access to the brain after systemic administration. Based on reports that growth factors can enter the brain after intranasal delivery, we investigated the effects of two such factors, fibroblast growth factor-2 (FGF-2) and heparin-binding epidermal growth factor-like growth factor (HB-EGF), on neurogenesis in the principal neuroproliferative regions of the adult mouse brain—the rostral subventricular zone (SVZ) and the subgranular zone (SGZ) of the hippocampal dentate gyrus. Here we report that intranasal administration of either FGF-2 or HB-EGF increases neurogenesis, Jin et al., Page 2 measured by the incorporation of bromodeoxyuridine (BrdU) into cells that express the early neuronal marker protein doublecortin (Dcx), in SVZ but not SGZ. These findings indicate that intranasal growth factors may have potential as neurogenesis-promoting therapeutic agents.

To determine if administration by the intranasal route would allow access of growth factors to neuroproliferative zones of the adult mouse brain, leading to increased neurogenesis, we studied two factors known to stimulate neurogenesis in the adult rat when injected into the cerebral ventricles—FGF-2 (Kuhn et al. (1997) *J. Neurosci.* 17: 5820-5829) and HB-EGF (Jin et al. (2002) *J. Neurosci.* 22: 5365-5373). These were given in two daily intranasal doses of 1 µg each for 1 week, during which mice also received two daily doses of BrdU, 50 mg/kg intraperitoneally, or saline vehicle. At the end of 1 week mice were killed, and brains were fixed, sectioned, and stained with antibodies against BrdU.

Figure 8A:
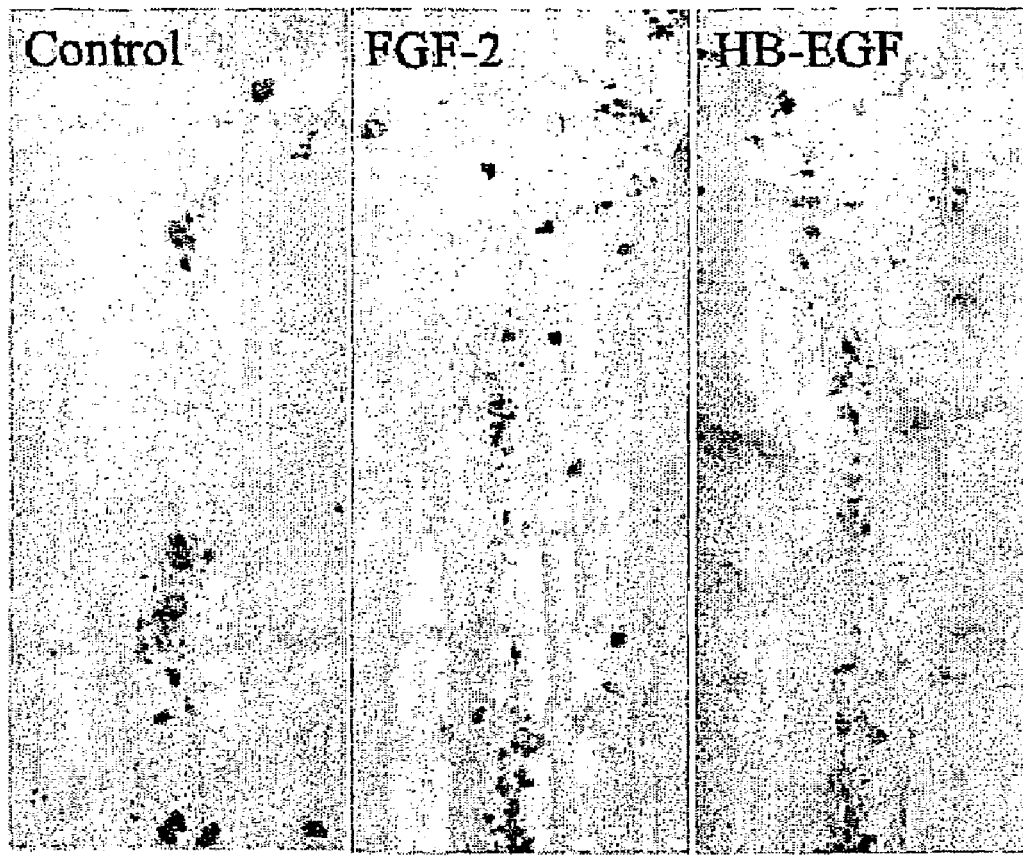
FIGS. 8A, 8B, and 8C show the effect of intranasal growth factors on BrdU labeling in neuroproliferative zones of adult mouse brain. Intranasal saline (Control), FGF-2 or HB-EGF and intraperitoneal BrdU were given and BrdU labeling was detected by immunohistochemistry in (FIG. 8A) SVZ and (FIG. 8B) SGZ. Cell counts showed an increase in BrdU-immunopositive cells induced by either FGF-2 or HB-EGF in SVZ but not SGZ (FIG. 8C). Data shown are representative fields (FIGS. 8A and 8B) or mean values±s.e.m., n=3.
Figure 8B:
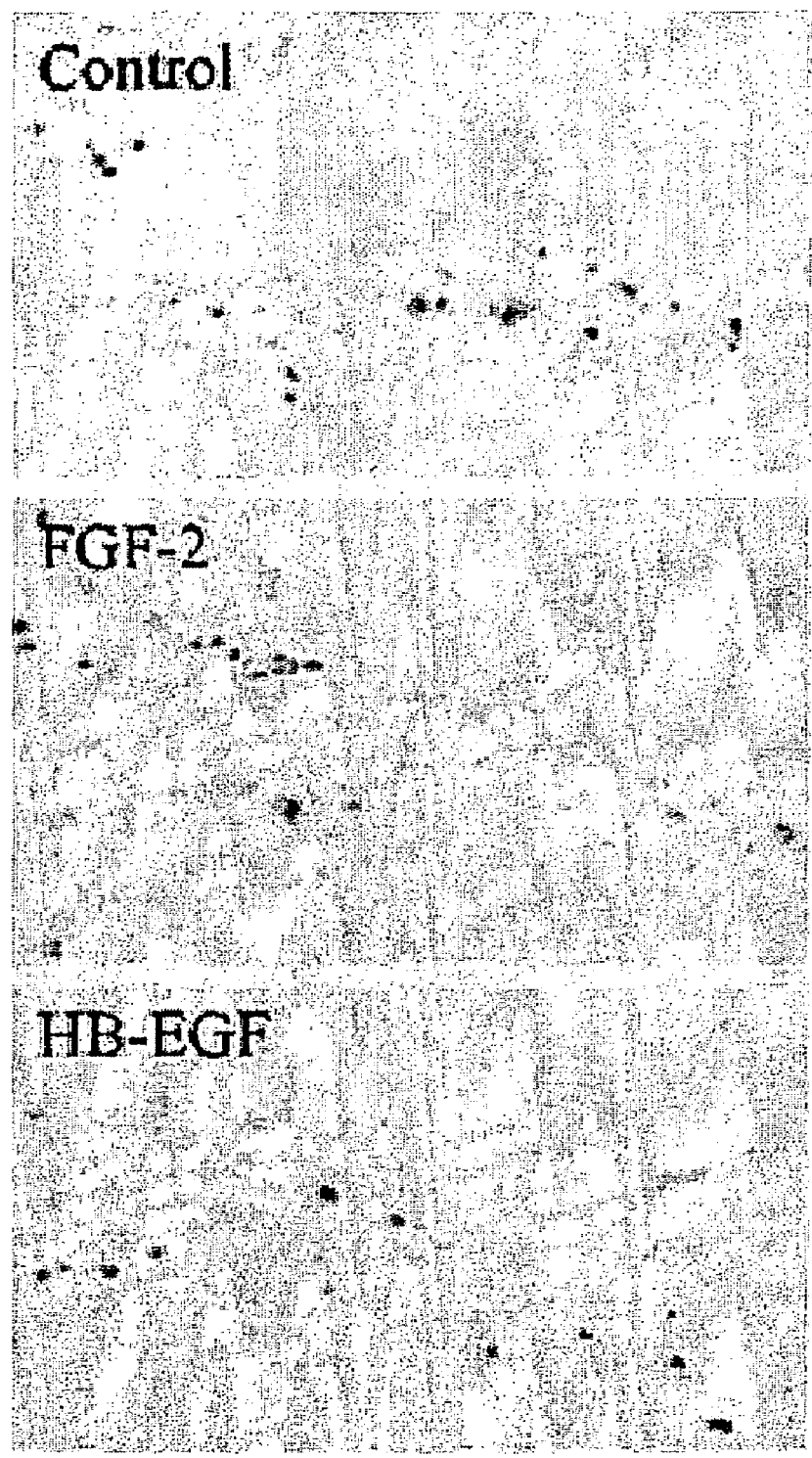
Figure 8C:
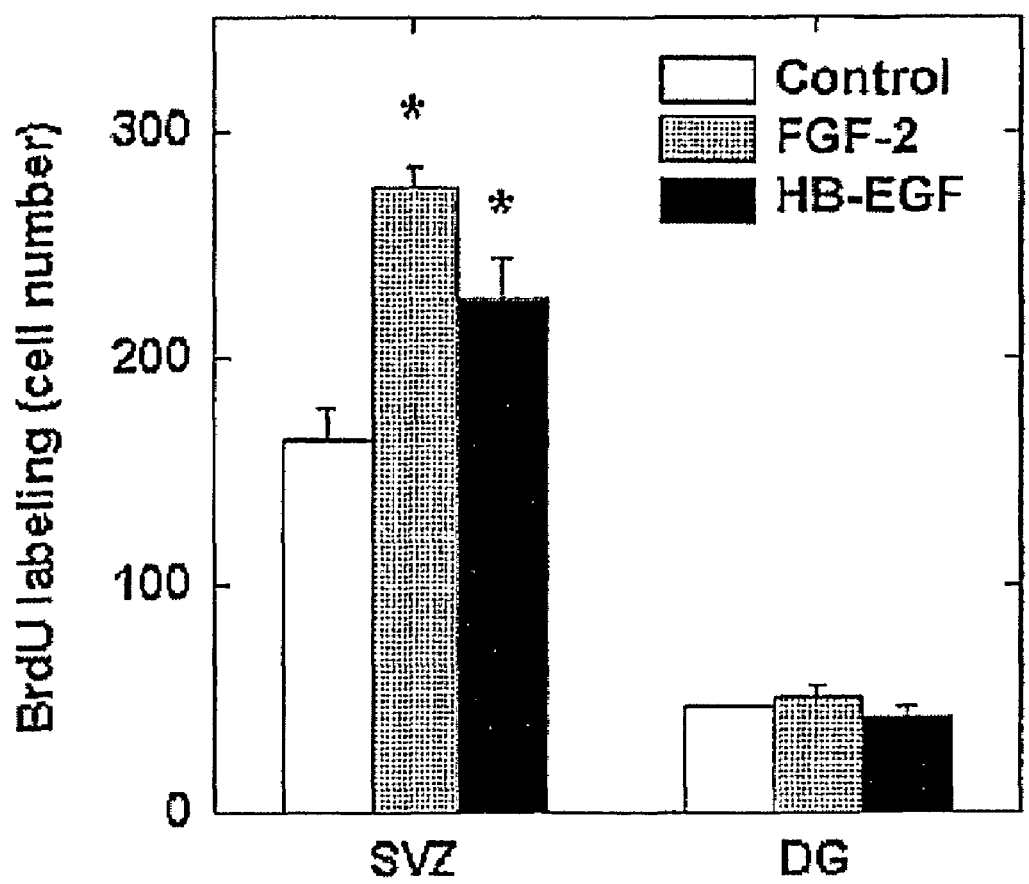

Consistent with previous results (Jin et al. (2002) *J. Neurosci.* 22: 5365-5373; Jin et al. (2001) *Proc. Natl. Acad. Sci. USA* 98: 4710-4715; Jin et al. (2002) *J. Clin. Invest.* 110: 311-319; Jin et al. (2002) *Proc. Natl. Acad. Sci. USA* 99: 11946-11950), control rats given no growth factors showed incorporation of BrdU into a modest number of cells in the SVZ and SGZ (FIG. 8). Following intranasal administration of FGF-2 or HB-EGF, BrdU labeling in the SVZ increased by ~70% and ~40%, respectively, whereas labeling in the SGZ was unaffected. More pronounced stimulation of neurogenesis in SVZ than SGZ has also been observed after intracerebroventricular administration of HB-EGF (Jin et al. (2002) *J. Neurosci.* 22: 5365-5373).

Figure 9A:
FIGS. 9A and 9B show the colocalization of BrdU and Dcx in SVZ of adult mouse brain after intranasal administration of FGF-2 (FIG. 9) or HB-EGF (FIG. 9B). Brain sections from mice treated with growth factors and BrdU were stained with antibodies against BrdU (red nuclei) and Dcx (green cytoplasm) and examined by double-label fluorescence immunohistochemistry with confocal imaging and three-dimensional reconstruction, which showed colocalization of BrdU and Dcx to the same cells. Data shown are representative fields (n=3).
Figure 9B:
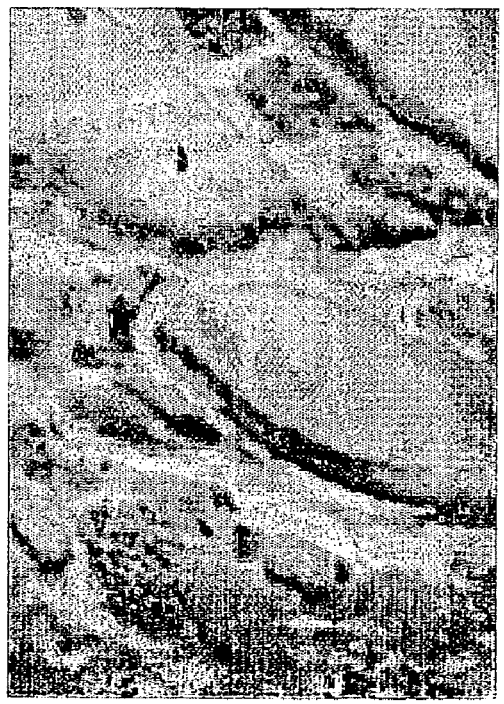

To determine the phenotype of SVZ cells that incorporated BrdU in response to FGF-2 or HB-EGF, brain sections were processed for double-label immunohistochemistry with antibodies against BrdU and against the early neuronal marker protein, Dcx (Francis et al. (1999) *Neuron* 23: 247-256; Gleeson et al. (1999) *Neuron* 23: 257-271). Dcx colocalized with BrdU in this region to a considerable extent (FIG. 9), indicating that many recently divided cells labeled with BrdU were of neuronal lineage. To confirm that growth factor treatment increased the absolute number of BrdU- and Dcx-immunopositive cells, we counted cells and calculated the percentage of BrdU-labeled cells that also expressed Dcx in SVZ from control and treated mice. Dcx-immunopositive cells accounted for 45±5% (n=3) of BrdU-labeled cells in control and 40±3% (n=5) of BrdU-labeled cells in treated mice (P=0.39). Taking into account the ~70% increase in BrdU labeling induced by FGF-2 and the 40% increase in labeling induced by HBEGF (see above), this translates to increases of ~50% (for FGF-2) and ~25% (for HB-EGF) in the absolute number of BrdU- and Dcx-immunopositive cells in SVZ of growth factor-treated mice.

Figure 10A:
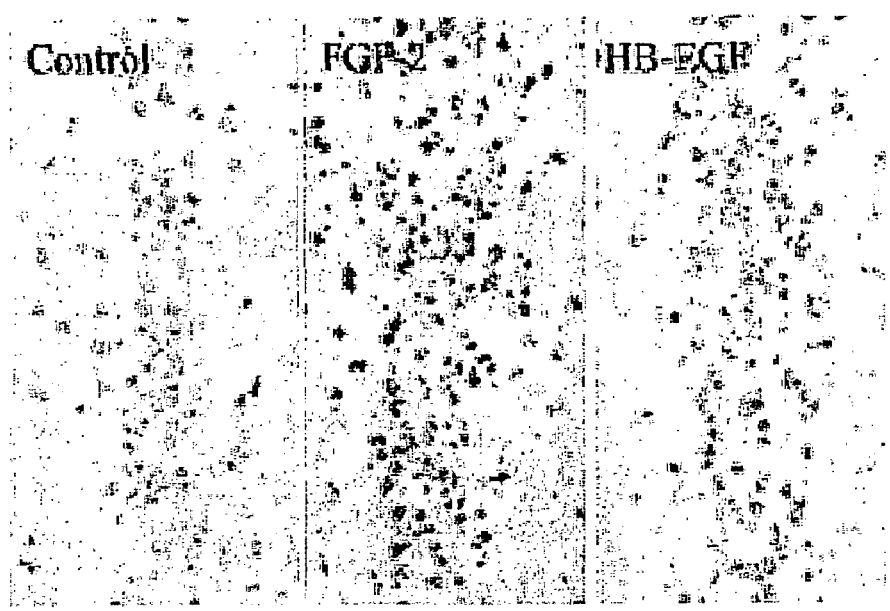
FIGS. 10A, and 10B show the effect of intranasal growth factors on BrdU labeling in olfactory bulb (OB) of adult mouse brain. Intranasal saline (Control), FGF-2 or HB-EGF and intraperitoneal BrdU were given and BrdU labeling was detected by immunohistochemistry in OB (FIG. 10A). Cell counts showed an increase in BrdU-immunopositive cells in OB induced by either FGF-2 or B-EGF (FIG. 10B). Data shown are representative fields (a) or mean values±s.e.m., n=6-12 (b). *, $P<0.05$ compared to Control (t-test).
Figure 10B:
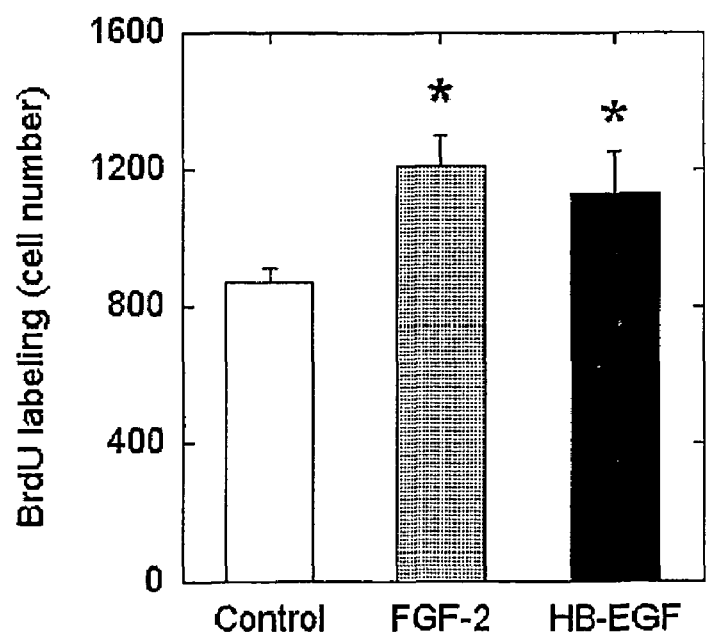

Neurons that arise in the SVZ of adult rodent brain normally migrate via the rostral migratory stream to the olfactory bulb (OB), where they replace interneurons undergoing rapid turnover (Luskin (1993) *Neuron* 11: 173-189; Lois et al. (1996) *Science* 271: 978-981). If the increased neurogenesis observed in the SVZ after growth factor administration is effectual, it should result in an increase in newly generated neurons reaching the OB. Therefore, we also counted BrdU-immunopositive neurons in the OB after treatment with intranasal FGF-2 or HB-EGF. BrdU-immunopositive cell counts in the OB increased by ~40% after FGF-2 and by ~30% after HB-EGF administration (FIG. 10), consistent with functional neurogenesis.

These findings demonstrate that growth factors administered by the intranasal route can stimulate neurogenesis in the adult mammalian brain. The persistence of neurogenesis in the adult brain suggests that newborn neurons might provide a source for the replacement of neurons destroyed by acute neurological catastrophes, such as stroke, or more insidious neurodegenerative processes, including Alzheimer's disease or Parkinson's disease (Homer and Gage (2000) *Nature* 407: 963-970). Several forms of experimental cerebral injury, including trauma (Gould and Tanapat (1997) *Neuroscience* 80: 427-436), seizures (Parent et al. (1997) *J. Neurosci.* 17: 3727-3378) and ischemia 3, stimulate neurogenesis, which could constitute an endogenous mechanism that promotes brain repair. Adult neurogenesis is responsive to a variety of growth factors, including epidermal growth factor 13, FGF-2 (Richards et al. (1992) *Proc. Natl. Acad. Sci. USA* 89: 8591-8595), insulin-like growth factor-I (IGF-I) (O'Kusky et al. (2000) *J. Neurosci.* 20: 8435-8442), erythropoietin (Shingo et al. (2001) *J. Neurosci.* 21" 9733-9743), HB-EGF 2, stem cell factor 4, and vascular endothelial growth factor (Jin et al. (2002) *Proc. Natl. Acad. Sci. USA* 99: 11946-11950). However, many of these large (~5-30 kD) molecules penetrate only poorly from the systemic circulation into the brain, and their limited bioavailability is a major impediment to therapeutic application (Thorne and Frey (2001) *Clin. Pharmacokinet.* 40: 907-946). For some growth factors, systemic administration is possible (Wagner et al. (1999) *J. Neurosci.* 19: 6006-6016; Aberg et al. (2000) *Neurosci.* 20: 2896-2903), but could present a risk of adverse systemic effects such as tumor angiogenesis or oncogenesis Talapatra and Thompson (2001) *J. Pharmacol. Exp. Ther.* 298, 873-878).

Several chemical agents appear to pass from the nasal cavity directly into the brain or cerebrospinal fluid by slow transneuronal or more rapid perineuronal pathways created by bipolar olfactory sensory neurons, axons of which penetrate the cribriform plate of the ethmoid bone to enter the olfactory bulb (Illum (2000) *Eur. J. Pharm. Sci.* 11: 1-18). For example, intranasal IGF-I enters the brain and improves outcome after focal cerebral ischemia in rats (Liu et al. (2001) *J. Neurol. Sci.* 187: 91-97), and melanocortin, vasopressin and insulin enter the cerebrospinal fluid, without first entering the bloodstream, in humans (Born et al. (2002) *Neurosci.* 5: 514-516). Which of these routes is employed by FGF-2 or HB-EGF to stimulate neurogenesis remains to be determined. However, the ability to enhance neurogenesis in the adult brain by noninvasive means may have therapeutic implications for neurological disease.

Methods

Growth Factor and BrdU Administration

Male CD1 mice weighing 30-40 g were given 20 µl of a 10 µg/ml solution of FGF-2 or HB-EGF into the right naris, 5 times at 5-min intervals, and this was repeated twice daily for 1 week. BrdU (Sigma, St. Louis, Mo.; 50 mg/kg) was dissolved in saline and given by the intraperitoneal route, twice daily with doses spaced 8 hr apart, for the same week. Animals were killed 24 hr after the final BrdU dose BrdU Immunohistochemistry Brains (5 per condition) were removed after perfusion with saline and 4% paraformaldehyde in PBS. Adjacent 50-μm sections, corresponding to coronal coordinates interaural 3.94 to 4.9 mm, bregma—0.14 to bregma—1.10 mm (SVZ) and interaural 1.26 to 2.46 mm, bregma—1.34 to bregma—2.54 (dentate gyrus), were cut with a cryostat and stored at −80° C. Sections were pretreated with 50% formamide, 280 mM NaCl and 30 mM sodium citrate at 65° C. for 2 hr, incubated in 2 M HCl at 37° C. for 30 min, and rinsed in 0.1 M boric acid (pH 8.5) at room temperature for 10 min. Sections were incubated in 1% H2O2 in PBS for 15 min, in blocking solution (2% goat serum, 0.3% Triton X-100 and 0.1% bovine serum albumin in PBS) for 2 hr at room temperature, and with 2 μg/ml of mouse monoclonal anti-BrdU antibody (Roche, Indianapolis, Ind.) at 4° C. overnight. Sections were washed with PBS, incubated with biotinylated goat-anti-mouse secondary antibody (Vector Laboratories, Burlingame, Calif.; 1:200) for 2 hr at 25° C., washed, and placed in avidin-peroxidase conjugate (Vector) solution for 1 hr. The horseradish peroxidase reaction was detected with 0.05% diaminobenzidine (DAB) and 0.03% H2O2. Processing was stopped with H2O and sections were dehydrated through graded alcohols, cleared in xylene, and coverslipped in permanent mounting medium (Vector). Sections were examined with a Nikon E300 epifluorescence microscope.

BrdU-immunopositive Cell Counts

BrdU-positive cells in SGZ and SVZ were counted blindly in 5-7 DAB-stained, 50-μm coronal sections per animal, spaced 200 μm apart. Cells were counted under high-power (200×) on a Nikon E300 microscope with Magnifire digital camera (ChipCoolers, Inc., Warwick, R.I.), and the image was displayed on a computer monitor. Results were expressed as the average number of BrdU-positive cells per section.

Double-label Fluorescence Immunohistochemistry

For double immunolabeling studies, sections were fixed with 4% paraformaldehyde in PBS for 1 hr at room temperature, washed twice with PBS, and incubated in 2 M HCl at 37° C. for 1 hr. After washing again, sections were incubated with blocking solution, then with primary antibodies at 4° C. overnight, and with secondary antibodies in blocking solution at room temperature for 2 hr. The primary antibodies used were mouse monoclonal anti-BrdU (Roche; 2 μg/ml) and affinity-purified goat polyclonal anti-Dcx (Santa Cruz Biotechnology, Santa Cruz, Calif.; 1:100); the secondary antibodies were rhodamine-conjugated rat-absorbed donkey anti-mouse IgG (Jackson ImmunoResearch; 1:200) and fluorescein isothiocyanate (FITC)-conjugated pig anti-goat IgG (Jackson ImmunoResearch; 1:200). Sections were mounted with Vectashield (Vector) and fluorescence signals were detected with a Nikon E800 microscope at excitation/emission wavelengths of 535/565 nm (rhodamine, red) and 470/505 (FITC, green). Results were recorded with a Magnifire digital camera (ChipCoolers). For confocal microscopy, a Nikon PCM-2000 laserscanning confocal microscope and Simple PCI imaging software (Compix, Cranberry Township, Pa.) were employed. Three-dimensional reconstructions were produced from 16-nm slices using Imaris software (Bitplane AG, Zurich, Switzerland).

Data Analysis

Quantitative data were expressed as mean±SEM from at least 3 experiments. Student's t test was used for statistical analysis, with P<0.05 considered significant.

It is understood that the examples and embodiments described herein are for illustrative purposes only and that various modifications or changes in light thereof are suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of mitigating one or more symptoms associated with acute or chronic neurodegenerative condition in a mammal, said method comprising:
   administering to said mammal stem cell factor in an amount sufficient to induce neuroproliferation from endogenous cells in said mammal.

2. The method of claim 1, wherein stem cell factor is intranasally administered.

3. The method of claim 1, wherein said stem cell factor is combined with a pharmaceutically acceptable excipient for nasal administration.

4. The method of claim 1, wherein said stem cell factor is formulated in a unit dosage formulation.

5. The method of claim 1, wherein said stem cell factor is administered as one of a plurality of growth factors.

6. The method of claim 1, wherein said mammal is a non-human mammal.

7. The method of claim 1, wherein said mammal is a human.

8. The method of claim 1, wherein said mammal is a mammal having or at risk for an acute or chronic neurodegenerative condition.

9. The method of claim 1, wherein said mammal is a mammal having an acute or chronic neurodegenerative condition.

10. The method of claim 8, wherein said acute or chronic neurodegenerative condition is a condition selected from the group consisting of Alzheimer's disease, Parkinson's disease, spinal cord injury, cranial injury, physical trauma to the head or spinal cord; a brain concussion; ischemic stroke caused by thrombosis or embolism; cerebral hemorrhage, general circulatory failure, circulatory disruption caused by cardiac arrest, hemodynamic shock caused by loss of blood due to injury or hemorrhage elsewhere in the body; vasculatory damage caused by vascular disease, bacterial infection, viral infection, fungal infection, cerebral or spinal tumors, glial cell swelling, hypoxic injury to the brain caused by respiratory disruption, and post-operative brain injury or stress.

11. The method of claim 1, wherein said administration is within 24 hours of an acute neurological trauma.

12. The method of claim 1, wherein said administration is within 1 week of an acute neurological trauma.

13. The method of claim 5, wherein said stem cell factor is administered with one or more additional neuroproliferative growth factors selected from the group consisting of heparin binding epidermal growth factor like growth factor (HB-EGF), and fibroblast growth factor-2.

* * * * *

UNITED STATES PATENT AND TRADEMARK OFFICE
CERTIFICATE OF CORRECTION

PATENT NO. : 7,605,128 B2
APPLICATION NO. : 10/503786
DATED : October 20, 2009
INVENTOR(S) : Greenberg et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1017 days.

Signed and Sealed this

Fifth Day of October, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,605,128 B2 | Page 1 of 1 |
| APPLICATION NO. | : 10/503786 | |
| DATED | : October 20, 2009 | |
| INVENTOR(S) | : Greenberg et al. | |

It is certified that error appears in the above-identified patent and that said Letters Patent is hereby corrected as shown below:

On the Title Page:

Column 1, item (75), line 1-2, entitled Inventors, change "David C. Greenberg, Sonoma, CA (US);" to -- David A. Greenberg, Sonoma, CA (US); --.

Column 1, line 16-19, change "This work was supported by Grants from The National Institute of Neurological Disorders and Stroke, National Institutes of Health. The Government of the United States of America may have certain rights in this invention." to -- This invention was made with Government support under Grant No. NS35965 awarded by The National Institute of Neurological Disorders and Stroke, National Institutes of Health. The Government has certain rights in this invention. --.

Signed and Sealed this
Fifth Day of April, 2011

David J. Kappos
*Director of the United States Patent and Trademark Office*